United States Patent
Hayakawa et al.

(10) Patent No.: US 10,618,789 B2
(45) Date of Patent: Apr. 14, 2020

(54) STERILIZATION PROCESS TRANSITION METHOD, PRODUCT FILLING APPARATUS, AND METHOD AND APPARATUS OF CLEANING AND STERILIZING THE PRODUCT FILLING APPARATUS

(71) Applicant: Dai Nippon Printing Co., Ltd., Tokyo (JP)

(72) Inventors: Atsushi Hayakawa, Tokyo (JP); Takaharu Hirooka, Tokyo (JP); Seiji Kuwano, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 0 days.

(21) Appl. No.: 15/777,738

(22) PCT Filed: Dec. 22, 2016

(86) PCT No.: PCT/JP2016/088420
§ 371 (c)(1),
(2) Date: May 21, 2018

(87) PCT Pub. No.: WO2017/111047
PCT Pub. Date: Jun. 29, 2017

(65) Prior Publication Data
US 2018/0334372 A1 Nov. 22, 2018

(30) Foreign Application Priority Data

Dec. 22, 2015 (JP) ................. 2015-249569
Apr. 7, 2016 (JP) ................. 2016-077362
Sep. 29, 2016 (JP) ................. 2016-191312

(51) Int. Cl.
| | |
|---|---|
| *B67C 3/00* | (2006.01) |
| *A61L 2/04* | (2006.01) |
| *B08B 9/027* | (2006.01) |
| *A61L 2/26* | (2006.01) |
| *B67C 7/00* | (2006.01) |

(52) U.S. Cl.
CPC ............... *B67C 3/001* (2013.01); *A61L 2/04* (2013.01); *A61L 2/26* (2013.01); *B08B 9/027* (2013.01);
(Continued)

(58) Field of Classification Search
CPC ..... A61L 2/04; A61L 2/26; B67C 3/00; B67C 7/00; B67C 3/001
See application file for complete search history.

(56) References Cited

U.S. PATENT DOCUMENTS

| | | |
|---|---|---|
| 2014/0286822 A1 | 9/2014 | Hayakawa |
| 2015/0291406 A1 | 10/2015 | Hayakawa et al. |

(Continued)

FOREIGN PATENT DOCUMENTS

| | | |
|---|---|---|
| JP | S61-50596 U | 4/1986 |
| JP | 2007-022600 A1 | 2/2007 |

(Continued)

OTHER PUBLICATIONS

International Publication No. WO 2014/098058 A1 corresponds to U.S. Patent Application Publication No. 2016/0185584 A1.

(Continued)

*Primary Examiner* — Sean E Conley
(74) *Attorney, Agent, or Firm* — Burr & Brown, PLLC

(57) ABSTRACT

A sterilization process transition method of switching from an SIP process to a product sterilization process in an apparatus including piping that feeds a product into a filling machine through a heating sterilization part. The process sterilizes the piping before a filling operation, and the product sterilization process sterilizes the product to be filled. An F value is calculated from temperature and flow-rate data on a fluid flowing in the heating sterilization part that are obtained from temperature sensors and flowmeters disposed in the product filling apparatus at predetermined (Continued)

time intervals. The temperature and flowrate at two or more predetermined positions in the product filling apparatus are adjusted from a set temperature and a set flowrate for the SIP process to a set temperature and a set flowrate for the product sterilization process while preventing the F value from becoming lower than a predetermined value.

11 Claims, 20 Drawing Sheets

(52) U.S. Cl.
CPC ............. *B67C 3/00* (2013.01); *B67C 7/00* (2013.01); *A61L 2202/23* (2013.01)

(56) References Cited

U.S. PATENT DOCUMENTS

| | | |
|---|---|---|
| 2016/0046475 A1 | 2/2016 | Hayakawa et al. |
| 2016/0185584 A1 | 6/2016 | Hayakawa et al. |

FOREIGN PATENT DOCUMENTS

| | | |
|---|---|---|
| JP | 2007-215893 A1 | 8/2007 |
| JP | 2011-255938 A1 | 12/2011 |
| JP | 2015-205734 A1 | 11/2015 |
| WO | 2014/098058 A1 | 6/2014 |
| WO | 2014/156724 A1 | 10/2014 |

OTHER PUBLICATIONS

International Publication No. WO 2014/156724 A1 corresponds to U.S. Patent Application Publication No. 2016/0046475 A1.
Japanese Patent Publication No. 2007-215893 A1.
Japanese Utility Model Laid-Open No. S61-50596 U.
Japanese Patent Publication No. 2007-022600 A1.
International Search Report and Written Opinion (Application No. PCT/JP2016/088420) dated Apr. 1, 2017.
Extended European Search Report (Application No. 16878933.7) dated Sep. 11, 2019.

STERILIZATION PROCESS TRANSITION METHOD, PRODUCT FILLING APPARATUS, AND METHOD AND APPARATUS OF CLEANING AND STERILIZING THE PRODUCT FILLING APPARATUS

BACKGROUND OF THE INVENTION

Field of the Invention

The present invention relates to a sterilization process transition method for an apparatus that fills a container such as a PET bottle with a drink as a product, a product filling apparatus that performs the sterilization process transition method, and a method and an apparatus of cleaning and sterilizing the product filling apparatus.

Description of Related Art

When an aseptic drink filling apparatus fills a container such as a bottle with a drink, not only does a product sterilization process in which the drink itself is sterilized to be aseptic have to be performed, but also product supply piping including a surge tank, a liquid feeding pipe, and filling nozzles in the product filling apparatus has to be cleaned and sterilized to be aseptic in advance.

Conventionally, with regard to the drink itself flowing in the product supply piping, the F value, which is a sterilization value, of the product is measured, and it is checked based on the historical information on the F value whether or not the product is sterilized to such an extent that the quality of the product can be assured (see Patent Documents 1 and 2, for example).

With the product supply piping of the aseptic drink filling apparatus, a CIP (Cleaning in Place) process and an SIP (Sterilizing in Place) process are performed regularly or each time the kind of drink is changed (see Patent Document 3, for example).

The CIP process is performed by passing a cleaner containing water and an alkali agent such as caustic soda as an additive through a flow path from the pipe line of the product supply piping to the filing nozzles of the filling machine and then passing a cleaner containing water and an acid agent as an additive. The CIP process is performed by circulating the cleaner in the product filling path while keeping the cleaner at 80° C. in a heating sterilization part. The CIP process removes a residue of the previous product in the product supply piping, for example (see Patent Document 3, for example).

The SIP process is a process to sterilize the interior of the product supply piping before the product filling operation is started, and is performed by passing a heated steam or hot water through the product supply piping cleaned by the CIP process described above, for example. The SIP process sterilizes the interior of the product supply piping and makes it aseptic (see Patent Document 3, for example).

When the product is passed through the product supply piping after the CIP process and the SIP process are performed, a product sterilization process is performed by heating and sterilizing the product in a heating sterilization part (UHT: Ultra High-temperature) arranged along the product supply piping. Then, a container such as a bottle can be filled with the sterilized product (see Patent Document 2, for example).

The CIP process, the SIP process and the product sterilization process take a long time, and there are various known methods of reducing the time. For example, as described in the patent documents listed below, there is a known method of performing the product sterilization process by determining the sterilization strength (F value) from the sterilization temperature and the flowrate.

PRIOR ART DOCUMENT

Patent Document

Patent Document 1: Japanese Utility Model Laid-Open No. 61-50596

Patent Document 2: Japanese Patent Laid-Open No. 2007-215893

Patent Document 3: Japanese Patent Laid-Open No. 2007-22600

SUMMARY OF THE INVENTION

Problems to be Solved by the Invention

By performing cleaning and sterilization of the product filling apparatus and sterilization of the product in the manner described above, the quality of the product can be properly and quickly assured.

However, if different processes such as the CIP process, the SIP process and the product sterilization process are performed in sequence, there is a problem that setting each process takes a very long time and it is difficult to reduce the time required for preparation for each process.

For example, when the product sterilization process for the product filling operation is started after the SIP process, in order to transition to the sterilization conditions for the manufacture, a temperature stabilization step needs to be performed by raising or lowering the temperature of the UHT heated for the SIP process to a desired set temperature or raising or lowering the flowrate of the product flowing in the product supply piping to a flowrate suitable for the bottle to be filled, while maintaining the aseptic condition. Conventionally, in the temperature stabilization step, the temperature or flowrate is controlled not to be out of the range between prescribed upper and lower limits over an extended time. This is intended to prevent the temperature or flowrate from being out of the range between the prescribed upper and lower limits due to a rapid decrease in temperature. If the temperature or flowrate is out of the range between the prescribed upper and lower limits, the aseptic condition of the product supply piping achieved by the SIP process cannot be maintained, so that the temperature or flowrate needs to be gradually reduced with care in the adjustment thereof. Specifically, after the flowrate is adjusted, the temperature of each stage of the heating part or cooling part of the UHT is carefully reduced. Setting each stage takes a long time, so that the temperature stabilization step takes a long time for the setting operation. In addition, if the temperature or flowrate goes out of the range between the prescribed upper and lower limits, the apparatus is poorly sterilized, and the SIP process needs to be performed again.

With the trend of energy saving in recent years, the large amount of thermal energy consumed in the temperature stabilization step performed in the transition from the SIP process to the product sterilization process has come to be perceived as a problem. The long time required for transition between processes also has come to be perceived as a problem from the viewpoint of production efficiency of the product.

An object of the present invention is to provide a sterilization process transition method and a product filling apparatus that can solve these problems.

According to a sterilization method that performs different processes such as the CIP process, the SIP process and the product sterilization process on the product supply piping of the product filling apparatus, when transitioning from the CIP process to the SIP process, a rinsing process is performed to rinse the cleaner used in the CIP process with aseptic water at room temperature. Therefore, as shown in FIG. 20, the temperature of the heating sterilization part decreases and thus needs to be raised to a temperature for the SIP process before the SIP process is started. Thus, there is a problem that the CIP process and the SIP process and the transition between the processes take a very long time. Furthermore, there is another problem that a switching operation including change of the UHT holding tube (swing bend), replacement and inspection of filters at different positions, and disassembly and cleaning of the homogenizer is performed between the CIP process and the SIP process and between the manufacturing step and the CIP process, and the switching operation takes a very long time.

As described above, according to the conventional cleaning and sterilization method, products cannot be manufactured during the CIP process or the SIP process, so that the operability of the product filling apparatus decreases, and the products cannot be efficiently manufactured. There is an intense demand for solving these problems.

The present invention has been devised to solve these problems, and an object of the present invention is to provide a method and an apparatus of cleaning and sterilizing a product filling apparatus that can efficiently manufacture products with an increased operability.

Means for Solving the Problems

The inventor has studied management of the F value in order to review the thermal energy required for switching from the SIP process to the product sterilization process or the required sterilization time for the drink supply piping of the aseptic filling apparatus. Then, the inventor has found that a setting change to a desired setting condition can be quickly made if the sterilization effect is determined in real time based not only on the time after a desired temperature is reached but also on an integration of the F value.

The present invention is based on the findings described above and is characterized by the following arrangements.

That is, a sterilization process transition method according to the present invention is a sterilization process transition method of switching from an SIP process to a product sterilization process in a product filling apparatus that includes product supply piping that feeds a product into a filling machine through a heating sterilization part, the SIP process being intended to sterilize the product supply piping in advance before a product filling operation, and the product sterilization process being intended to sterilize the product to be filled, wherein an F value is calculated from temperature data and flowrate data on a fluid flowing in the heating sterilization part that are obtained from a plurality of temperature sensors and flowmeters disposed at arbitrary positions in the product filling apparatus at predetermined time intervals, and the temperature and flowrate at two or more of the plurality of predetermined positions in the product filling apparatus are adjusted from a set temperature and a set flowrate for the SIP process to a set temperature and a set flowrate for the product sterilization process while preventing the F value from becoming lower than a predetermined value.

In the sterilization step transition method according to the present invention, it is preferable that a pressure of the product passing through the heating sterilization part is higher than a pressure of a heat source that heats the heating sterilization part or a pressure of a coolant that cools the heating sterilization part.

In the sterilization process transition method according to the present invention, the F value may be calculated according to $$F = \int_{t_0}^{t_1} 10^{(T-Tr)/Z} dt \quad \text{[formula 1]}$$

where T denotes an arbitrary sterilization temperature (° C.), $10^{(T-Tr)/Z}$ represents a fatality rate at an arbitrary temperature T, Tr denotes a reference temperature r (° C.), and Z denotes a Z value (° C.).

A product filling apparatus according to the present invention is a product filling apparatus comprising product supply piping that feeds a product into a filling machine through a heating sterilization part and a sterilization process transition unit that switches from an SIP process to a product sterilization process, the SIP process being intended to sterilize the product supply piping in advance before a product filling operation, and the product sterilization process being intended to sterilize the product to be filled, wherein the product filling apparatus further comprises a controller that calculates an F value from temperature data and flowrate data on a fluid flowing in the heating sterilization part that are obtained from a plurality of temperature sensors and flowmeters disposed at arbitrary positions in the product filling apparatus at predetermined time intervals, and adjusts the temperature and flowrate at two or more of the plurality of predetermined positions in the product filling apparatus from a set temperature and a set flowrate for the SIP process to a set temperature and a set flowrate for any one of the product sterilization processes while preventing the F value from becoming lower than a predetermined value.

A method of cleaning and sterilizing a product filling apparatus according to the present invention is a method of cleaning and sterilizing a product filling apparatus that includes product supply piping that feeds a product into a filling machine through a heating sterilization part, the method comprising a CIP process of removing a remaining foreign matter from a product or the like on an interior of the product supply piping and an SIP process of sterilizing the interior of the product supply piping, wherein the CIP process and the SIP process are performed at the same time or in sequence without an interruption between the CIP process and the SIP process.

In the method of cleaning and sterilizing a product filling apparatus according to the present invention, it is preferable that the SIP process ends when an F value reaches a predetermined value, the F value being determined by substituting a value obtained from a thermometer in the product supply piping into the following formula:

$$F = \int_{t_0}^{t_1} 10^{(T-121.1)/10} dt \quad \text{[formula 2]}$$

where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

In the method of cleaning and sterilizing a product filling apparatus according to the present invention, it is preferable that rinse water used to rinse a cleaner used in the CIP process has a sterilization strength determined from a sterilization temperature of the heating sterilization part and a flowrate in the heating sterilization part.

In the method of cleaning and sterilizing a product filling apparatus according to the present invention, it is preferable that the method comprises a first manufacturing step of performing a filling step of filling a container with the product while performing a product sterilization process after the SIP process, and a second manufacturing step including the CIP process and the SIP process for manufacturing a product different from that manufactured in the first manufacturing step, and the first manufacturing step and the second manufacturing step are performed without reducing the temperature of the heating sterilization part to be equal to or lower than a set temperature of the CIP process.

In the method of cleaning and sterilizing a product filling apparatus according to the present invention, it is preferable that the product supply piping is provided with a filtering device that filters the product, and the filtering device includes a switching step of switching between a first filtering device used in at least the first manufacturing step and a second filtering device used in the second manufacturing step.

In the method of cleaning and sterilizing a product filling apparatus according to the present invention, it is preferable that the first manufacturing step includes a cleaning step of removing a remaining foreign matter on the second filtering device.

A product filling apparatus according to the present invention is a product filling apparatus that comprises product supply piping that feeds a product into a filling machine through a heating sterilization part and performs a CIP process of removing a remaining foreign matter from a product or the like on an interior of the product supply piping and an SIP process of sterilizing the interior of the product supply piping, wherein the CIP process and the SIP process are performed at the same time or in sequence without an interruption between the CIP process and the SIP process.

Effects of the Invention

According to the present invention, in switching from the SIP process for the product supply piping of the product filling apparatus to the product sterilization process, the F value is integrated in real time, and the temperature and the flowrate at two or more of a plurality of positions in the product filling apparatus are adjusted to the set temperature and the set flowrate for the subsequent product sterilization process while controlling the F value not to be lower than a predetermined value. Therefore, compared with prior art, the transition from the SIP process for the product supply piping of the product filling apparatus to the product sterilization process can be more properly and quickly achieved, the product filling operation can be started earlier, the time between productions of different products for changing products can be reduced, and the production efficiency can be improved.

According to the present invention, in the sterilization of the product filling apparatus, after the CIP process using a cleaner, the SIP process is started without stopping the liquid feed pump, and the product supply piping is rinsed with aseptic water used in the SIP process. Therefore, the time required for transition from the CIP process to the SIP process can be reduced. In addition, water is not discharged after the CIP process and reused for the subsequent SIP process, so that significant water conservation can be achieved. In addition, the rise in temperature required to perform the SIP process is small (or zero), so that the required vapor energy can be substantially reduced.

According to the present invention, the sterilization by the SIP process is assured based on the actual sterilization strength (F value) determined from the sterilization temperature and the flowrate. Therefore, compared with the conventional sterilization method in which temperature and sterilization time are managed, the SIP process can be more properly and quickly performed, the product filling operation can be started earlier so that the time required for changing products can be reduced, and the products can be efficiently manufactured.

According to the present invention, the first manufacturing step including the CIP process, the SIP process and the product sterilization process and the second manufacturing step in which the CIP process, the SIP process and the product sterilization process are performed to perform filling with a product different from that in the first manufacturing step are performed in succession, even if the product filling apparatus manufactures products while changing the kind of product, the product filling apparatus can efficiently manufacture products with an increased operability.

According to the present invention, the product supply piping includes a first filtering device and a second filtering device. Therefore, these filtering devices can be efficiently washed by washing the second filtering device while the first filtering device is used in the first manufacturing step (see FIG. 5).

DETAILED DESCRIPTION OF THE INVENTION

First Embodiment

In the following, a first embodiment of the present invention will be described with reference to the drawings.

A structure of a product filling apparatus will be first described, and a method of sterilizing the apparatus and a method of switching between processes will then be described.

Figure 1:
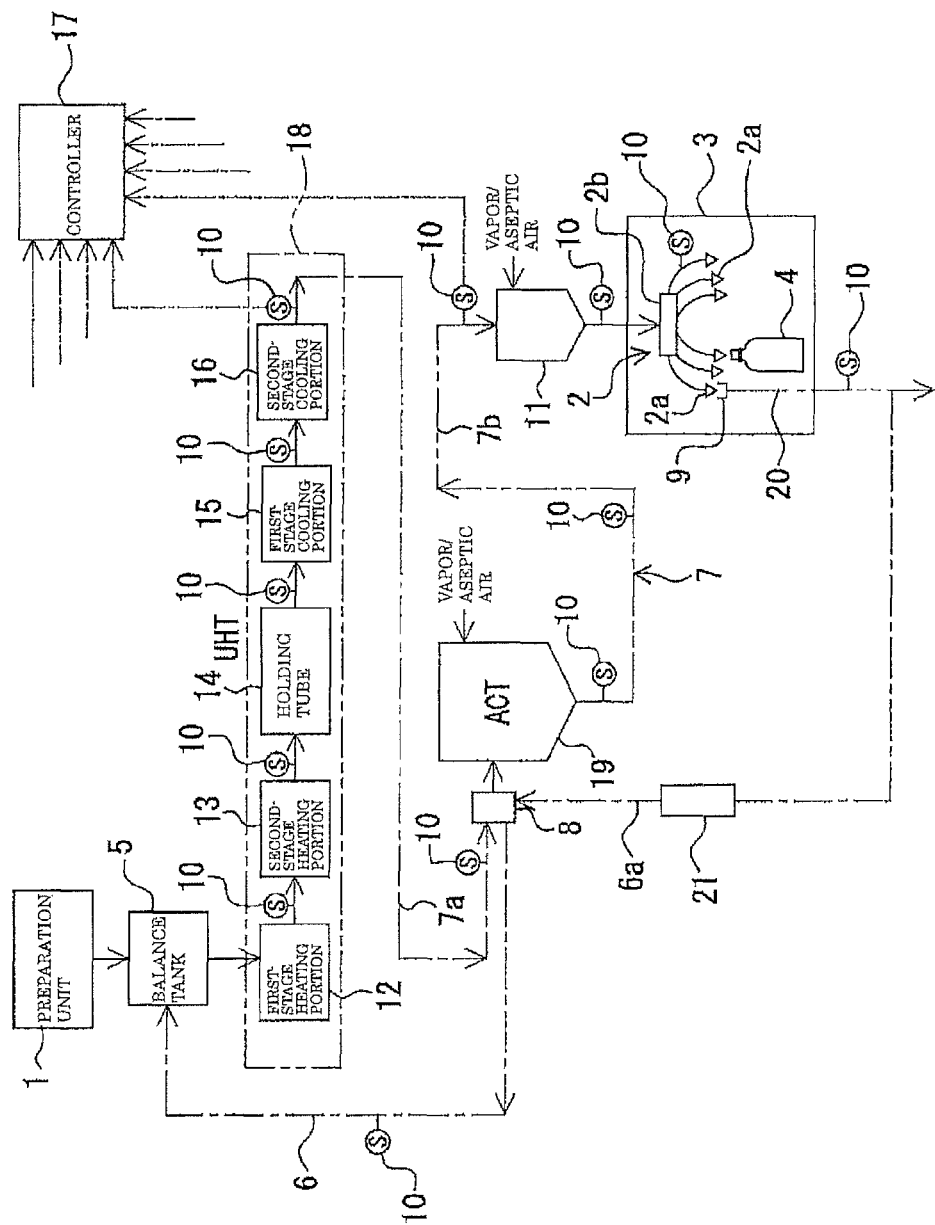
FIG. 1 is a block diagram showing a product filling apparatus according to a first embodiment of the present invention.

As shown in FIG. 1, the product filling apparatus includes a preparation unit 1 for a drink as a product and a filling machine 2 that fills a bottle 4 with the drink. The preparation unit 1 and filling nozzles 2a in the filling machine 2 are coupled to each other by product supply piping 7. The filling machine 2 is surrounded by an aseptic chamber 3.

The preparation unit 1 prepares a drink such as tea or fruit juice by mixing ingredients in desired proportions. The preparation unit 1 is a well-known device and therefore will not be described in detail herein.

The filling machine 2 includes a large number of filling nozzles 2a arranged around a wheel (not shown), which rotates at high speed in a horizontal plane. As the wheel rotates, the filling nozzles 2a rotate, and the drink is metered from the filling nozzles 2a to bottles 4 traveling below the filling nozzles 2a at a velocity adjusted to the circumferential velocity of the wheel. The filling machine 2 is also a well-known machine and therefore will not be described in detail herein.

In the product filling apparatus, along the path of the product supply piping 7 from the preparation unit 1 to the filling machine 2, a balance tank 5, a heating sterilization part (hereinafter, referred to as UHT: Ultra High-temperature) 18, a manifold valve 8, an aseptic surge tank 19, and a head tank 11 are disposed in this order from upstream to downstream of the flow of the drink.

The UHT 18 includes a first-stage heating portion 12, a second-stage heating portion 13, a holding tube 14, a first-stage cooling portion 15 and a second-stage cooling portion 16, for example. The drink or water supplied from the balance tank 5 is gradually heated while fed from the first-stage heating portion 12 to the second-stage heating portion 13 until a target sterilization temperature is reached at an exit of the second-stage heating portion 13, kept at the sterilization temperature for a certain time in the holding tube 14, and then gradually cooled while fed from the first-stage cooling portion 15 to the second-stage cooling portion 16. The number of stages of heating portions or cooling portions can be increased or decreased as required. The UHT 18 may include a homogenizer capable of automatic washing. The homogenizer is preferably disposed between the first-stage heating portion and the second-stage heating portion or between the first-stage cooling portion and the second-stage cooling portion where the temperature of the content of the product is about 50 to 70° C. In the former case, a common homogenizer can be used. In the latter case, however, an aseptic homogenizer is needed.

The balance tank 5, the manifold valve 8, the aseptic surge tank 19 and the head tank 11 are well-known devices and therefore will not be described in detail herein.

Next, a process path along which a CIP process and an SIP process are performed will be described. As shown by a bold line in FIG. 2, an upstream-side piping section 7a of the product supply piping 7, which extends from the balance tank 5 to the manifold valve 8 through the UHT 18, is provided with a feedback path 6 to form an upstream-side process path, which is a circulation path for the CIP process or SIP process. As shown by a bold line in FIG. 3, a downstream-side piping section 7b, which extends from the manifold valve 8 to the aseptic surge tank 19, then to the head tank 11, then to the filling machine 2 and then back to the manifold valve 8, is provided with a feedback, path 6a to form a downstream-side process path, which is a circulation path for the CIP or SIP process.

The upstream-side piping section 7a is provided with temperature sensors 10 at positions including a position where the temperature is less likely to increase when hot water or the like is supplied to the interior thereof. For example, the temperature sensors 10 can be disposed at positions along the pipe line from the first-stage heating portion in the UHT 18 to the manifold valve 8, such as positions in the UHT 18, a position at the outlet of the second-stage cooling portion 16, and a position at the inlet of the manifold valve 8. The temperature sensors 10 are disposed at these positions. Temperature information from the temperature sensors 10 is transmitted to a controller 17.

The balance tank 5 can be any tank, such as an open tank for which the filling temperature is prescribed to be lower than 100° C. or a tank that is a first class pressure vessel to which a fluid at a temperature of 100° C. or higher can be fed. When the open tank is used, a cooling unit is preferably provided between the manifold valve 8 and the balance tank 5.

Figure 3:
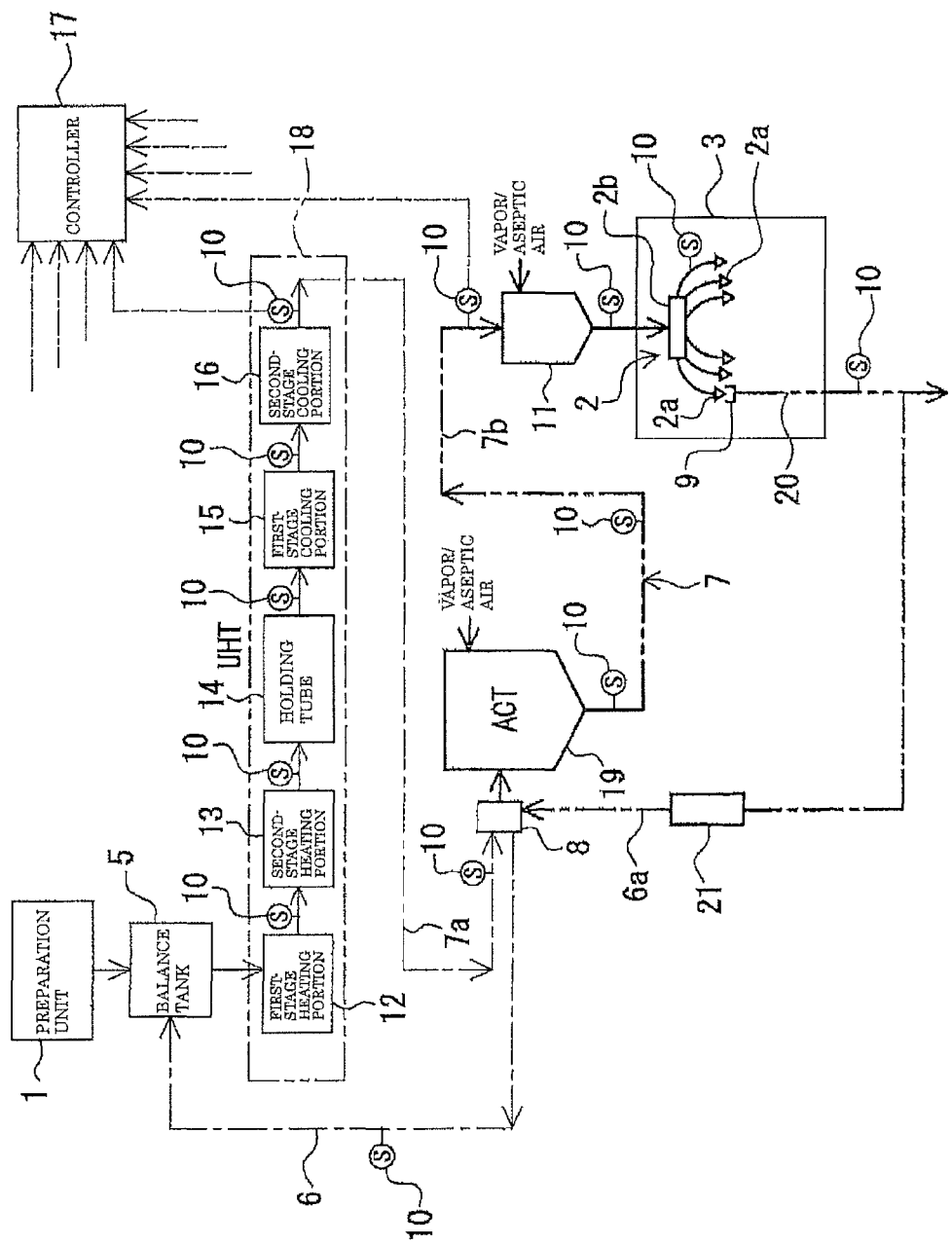
FIG. 3 is a block diagram for illustrating the SIP process performed for a downstream-side piping section of the product supply piping in the product filling apparatus between the aseptic surge tank (ACT) (inclusive) and filling nozzles (inclusive).

As shown by the bold line in FIG. 3, the downstream-side piping section 7b of the product supply piping 7, which is located downstream of the upstream-side piping section 7a and extends from the manifold valve 8 to the filling machine 2 through the aseptic surge tank 19 and the head tank 11, is also provided with temperature sensors 10 at positions including a position where the temperature is less likely to increase when heated steam or the like is supplied to the interior thereof. For example, the temperature sensors 10 can be disposed at positions along the pipe line from the aseptic surge tank 19 to the filling nozzles 2a, such as a position in the vicinity of the outlet of the aseptic surge tank 19, a midway bent point, positions in the vicinities of the inlet and outlet of the head tank 11, positions between a manifold 2b and the filling nozzles 2a in the filling machine 2. The temperature sensors 10 are disposed at these positions. Temperature information from the temperature sensors 10 is transmitted to the controller 17. The downstream-side piping section 7b, which extends from the filling machine 2 downstream of the aseptic surge tank 19 and the head tank 11 to the manifold valve 8, is provided with the feedback path 6a to form a circulation path for the CIP process or SIP process.

In the downstream-side piping section 7b, a cup 9 is provided for an opening of each filling nozzle 2a in the filling machine 2 for the CIP process or SIP process, and the cup 9 can be brought closer to and separated from the filling nozzle 2a. To perform the CIP process or SIP process, an actuator (not shown) puts each cup 9 on the opening at the tip end of the filling nozzle 2a in the filling machine 2 to connect a leading end of a drain tube 20 to the opening of the filling nozzle 2a.

The product supply piping 7 can include various switching valves, pumps or other components in addition to the manifold valve 8 and the actuator (not shown), and these components are also controlled by the controller 17.

Next, a method of sterilizing the product filling apparatus described above and a method of transition from the SIP process to a product sterilization process will be described with reference to FIGS. 2 to 4.

Figure 2:
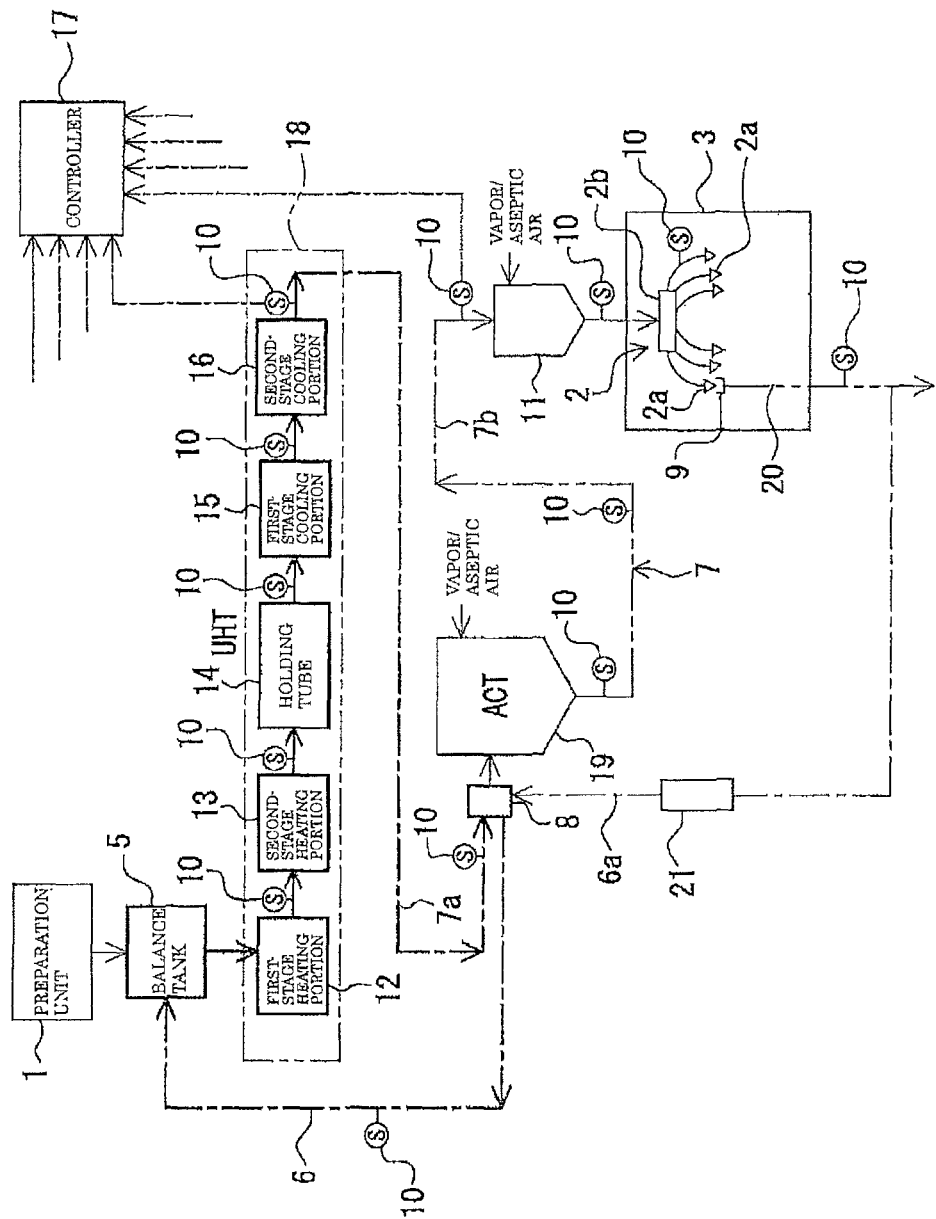
FIG. 2 is a block diagram for illustrating an SIP process performed for a section of product supply piping in the product filling apparatus between a heating sterilization part (inclusive) and an aseptic surge tank (ACT) (exclusive).

(1) When an operation button on a panel (not shown) of the controller 17 is manipulated, the SIP process is performed for each of the upstream-side piping section 7a and the downstream-side piping section 7b of the product supply piping 7 in a predetermined procedure (see FIGS. 2 and 3). Before the SIP process is started, the manifold valve 8 disconnects the upstream-side piping section 7a and the downstream-side piping section 7b from each other.

The SIP process for the upstream-side piping section 7a and the SIP process for the downstream-side piping section 7b can be performed in sequence or in parallel with each other.

(2) First, water is fed from a water supply source (not shown) to the interior of the circulation path through the balance tank 5. The water is heated and sterilized in the UHT 18 while circulating in the circulation path. In this way, the interior of the upstream-side piping section 7a is sterilized.

(3) When the hot water is flowing in the upstream-side piping section 7a, the temperature sensors 10 disposed at different positions along the upstream-side piping section 7a transmit temperature information to the controller 17 at regular time intervals. In this embodiment, it is assumed that the drink, which is a product liquid with which a bottle b is filled, has a pH of 4.6 or higher, a reference temperature Tr is 121.1° C., and the Z value is 10° C.

When the temperature at each of the different positions raised by heating by the hot water reaches 121.1° C., the controller starts calculating the F value at the position according to the following formula.

$$F = \int_{t_0}^{t_1} 10^{(T-121.1)/10} dt \quad \text{[formula 3]}$$

where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

When the minimum F value of the F values calculated according to the formula described above reaches a target value, it is determined that sterilization of the upstream-side piping section 7a is completed, cooling water is supplied to the first-stage cooling portion 15 and the second-stage cooling portion 16, and the hot water is thereby cooled and continuously circulates, waiting for the start of sterilization of the drink.

After the SIP process is completed, a temperature stabilization step is performed to set the temperature and flowrate of the product supply piping for the product sterilization process for the drink.

In the temperature stabilization step, the sterilization temperatures at the positions in the UHT 18 and the time required for the water to pass through the holding tube 14 are recorded at intervals of 1 second. The temperature data and the flowrate data are transmitted to the controller 17 and stored. The temperature data and the flowrate data are preferably recorded for a period of time (for example, 200 seconds) that is three or four times as long as the passing time of the holding tube 14 (for example, 60 seconds).

The controller 17 calculates the sterilization strength (F value) from the passing time and the sterilization temperature for the UHT 18 (the temperature at the outlet of the tube) in real-time. While monitoring the calculated F value, the controller 17 adjusts the temperature and flowrate at each position (from the first-stage heating portion 12 to the second-stage cooling portion 16) to the set value for the product sterilization process. The temperatures and flowrates at all the positions from the first-stage heating portion 12 to the second-stage cooling portion 16 may be adjusted at the same time, or the temperatures and flowrates at two or more of the positions from the first-stage heating portion 12 to the second-stage cooling portion 16, for example, may be adjusted at the same time.

If the pressure of the product passing through the UHT 18 is lower than the pressure of the heat source that heats the UHT 18 or the coolant that cools the UHT 18, poor sterilization can occur. From the viewpoint of safe back pressure, the pressure of the product passing through the UHT 18 is adjusted and set to be greater than the pressure of the heat source that heats the UHT 18 or the coolant that cools the UHT 18.

According to the transition method, even if the sterilization temperature is momentarily lower than a lower limit, for example, an actual sterilization strength (F value) is assured, so that poor sterilization does not occur, and transition to the product sterilization process can properly and quickly occur.

In the formula for calculating the F value described above, the reference temperature Tr and the Z value can be changed according to the kind of the drink, which is a product liquid.

For example, when the pH of the product liquid is equal to or higher than 4 and lower than 4.6, the reference temperature Tr can be 85° C., and the Z value can be 7.8° C. When the pH of the product liquid is lower than 4, the reference temperature Tr can be 65° C., and the Z value can be 5° C.

The values to be substituted into the formula described above can be changed as appropriate according to the ease of development of microorganisms, the temperature during distribution or the like of the product liquid, such as tea, mineral water or a chilled drink.

(4) After that, the product is fed from the preparation unit 1 to the balance tank 5, and sterilization of the product is started. Once the product replaces the water, the upstream-side piping section 7a is disconnected from the feedback path, and sterilized product is stored in the aseptic surge tank 19.

(5) When or before the SIP process for the upstream-side piping section 7a is started, the SIP process of the downstream-side piping section 7b including the aseptic surge tank 19 is started.

First, the cup 9 is put on the opening of the filling nozzle 2a, the drain tube 20 is connected to the filling nozzle 2a, and then heated steam is supplied into the aseptic surge tank 19 and the head tank 11 from a heated steam supply source (not shown).

The heated steam flows from the aseptic surge tank 19 to the filling nozzles 2a through the downstream-side piping section 7b and heats those components before being discharged out of the filling machine 2 through the drain tubes 20. If water is used for the SIP process for the downstream-side piping section 7b as with the SIP process for the upstream-side piping section 7a, water is fed from the water supply source (not shown) to the circulation path through the aseptic surge tank 19, and the water is heated and sterilized by a heating unit 21 while circulating in the circulation path including the feedback path 6a. In this way, the downstream-side piping section 7b is sterilized by the warm water or hot water. The sterilization method based on the F value is the same as the sterilization method for the upstream-side piping section 7a and therefore will not be described in detail herein.

(6) While the heated steam is flowing in the downstream-side piping section 7b, the temperature sensors 10 disposed at different positions in the downstream-side piping section 7b transmit temperature information to the controller 17 at regular time intervals.

When the temperature raised by heating by the heated steam reaches 121.1° C. at each position, the controller 17 calculates the F value at the position according to the formula described above.

When the minimum F value of the calculated F values reaches a target value, supply of the heated steam to the aseptic surge tank 19 and the interior of the downstream-side piping section 7b is stopped. The time required for the SIP for the downstream-side piping section 7b is substantially reduced compared with the conventional SIP process.

(7) After that, aseptic air or aseptic water is fed into the downstream-side piping section 7b to cool the interior of the downstream-side piping section 7b to, for example, room temperature. Then, the drain tubes 20 are disconnected. Furthermore, the actuator (not shown) removes the cups 9 from the openings of the filling nozzles 2a. The aseptic water may be fed from the product sterilizer that has finished the SIP process and is in the water operation in the standby state. Alternatively, aseptic water from a bottle rinser (not shown) may be received through the manifold valve 8 and used for cooling. The cooling with the aseptic water can be started after the temperature of the tank after the SIP process has been reduced to below 110° C. by cooling with the aseptic air. The operation of supplying the aseptic water is performed by supplying aseptic air to prevent the pressure in the tank from decreasing due to rapid cooling by using an intermittent timer. After the temperature of the tank has decreased to about 30 to 90° C., and the cooling is completed, the aseptic water remaining in the tank and the piping is blown off by aseptic air while maintaining a positive pressure, and the product is received. By additionally using the aseptic water, the downstream-side piping section 7b can be cooled in a shorter time than when the downstream-side piping section 7b is cooled only by air.

(8) After the SIP process for the aseptic surge tank 19 and the following part of the downstream-side piping section 7b ends, the drink flowing from the heating sterilizing part 18 through the upstream-side piping section 7a is stored in the aseptic surge tank 19, and the bottles 4 start being filled with the drink flowing therefrom through the downstream-side piping section 7b.

The same temperature stabilization step as that for the upstream-side piping section 7a described above can be performed for the downstream-side piping section 7b to achieve proper and quick transition from the SIP process to the product sterilization process.

Figure 4:
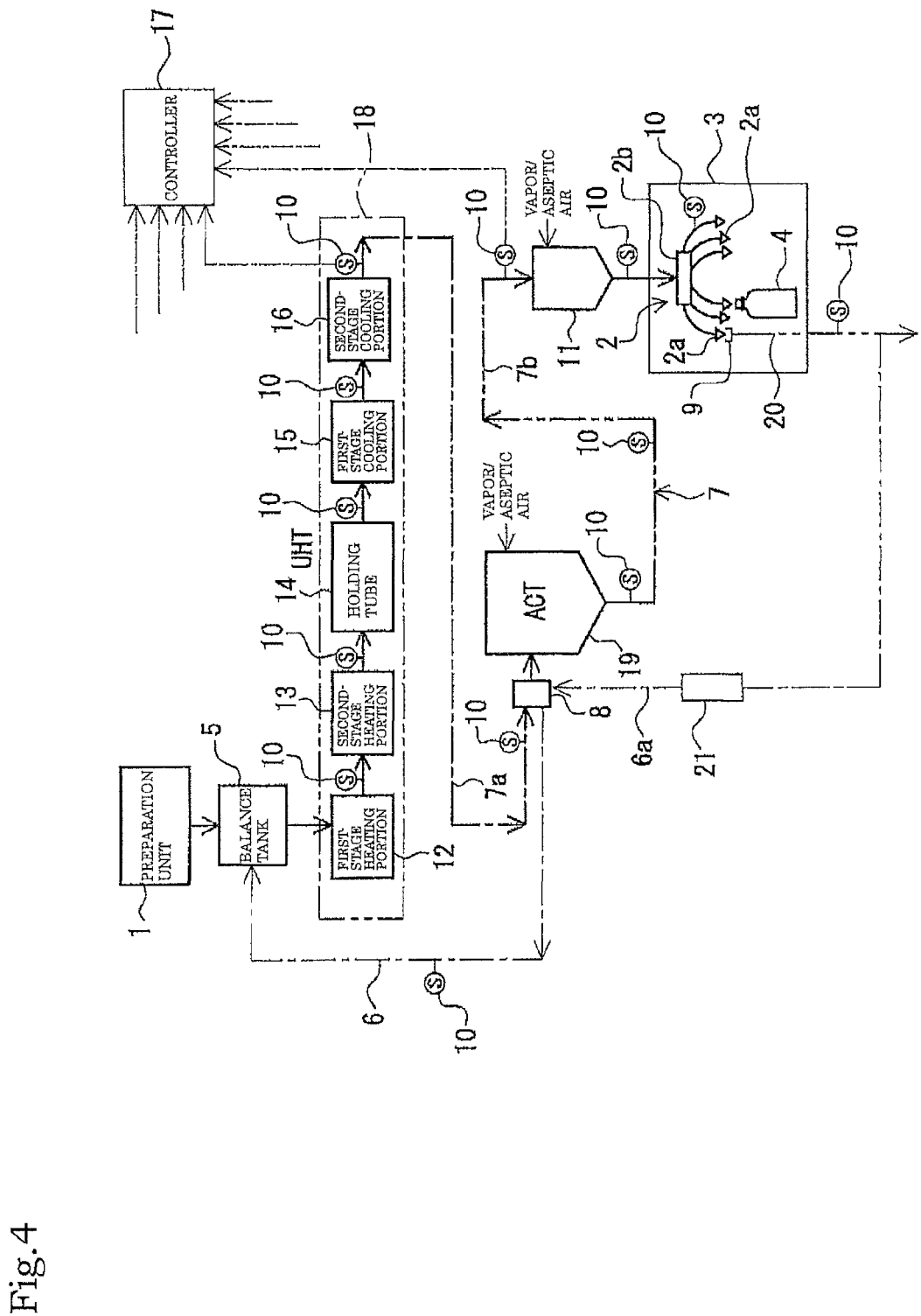
FIG. 4 is a block diagram for illustrating production of a bottled product.

As shown by a bold line in FIG. 4, the product prepared in the preparation unit 1 flows to the interior of the filling machine 2 through the sterilized upstream-side piping section 7a and downstream-side piping section 7b of the product supply piping 7, and the bottles 4 as containers are filled with the drink through the filling nozzles 2a in the filling machine 2. The bottles 4 filled with the product are capped by a capper (not shown) and then fed out of the filling machine 2.

Second Embodiment

Next, a method of cleaning and sterilizing the product filling apparatus and a method of transition from the CIP process to the SIP process according to a second embodiment will be described with reference to FIGS. 6 to 19.

(CIP Process)

Figure 6:
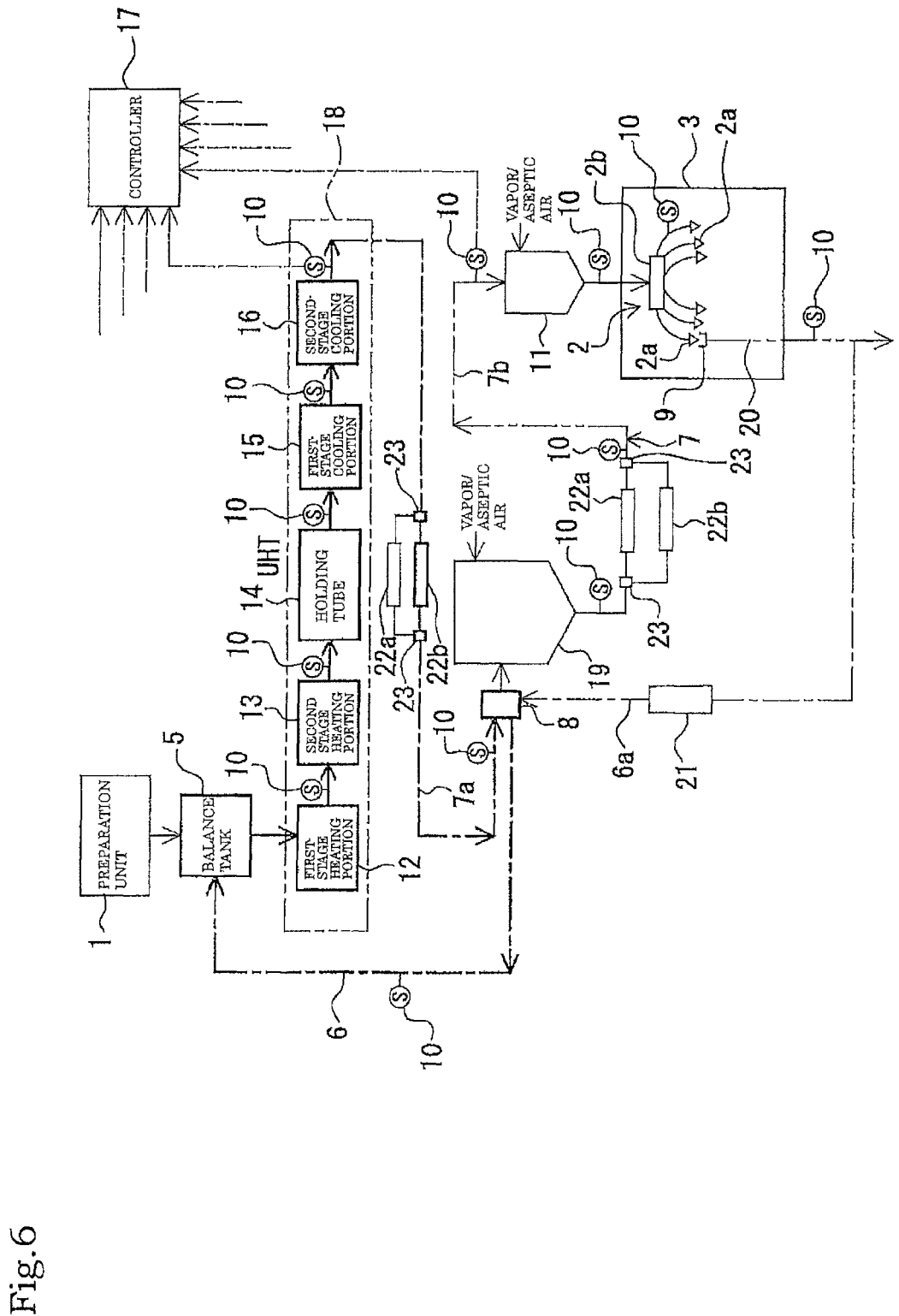
FIG. 6 is a block diagram for illustrating a CIP process or SIP process performed for an upstream-side piping section of product supply piping between a heating sterilization part (inclusive) and an aseptic surge tank (exclusive) in the cleaning and sterilization method according to the second embodiment of the present invention.
Figure 7:
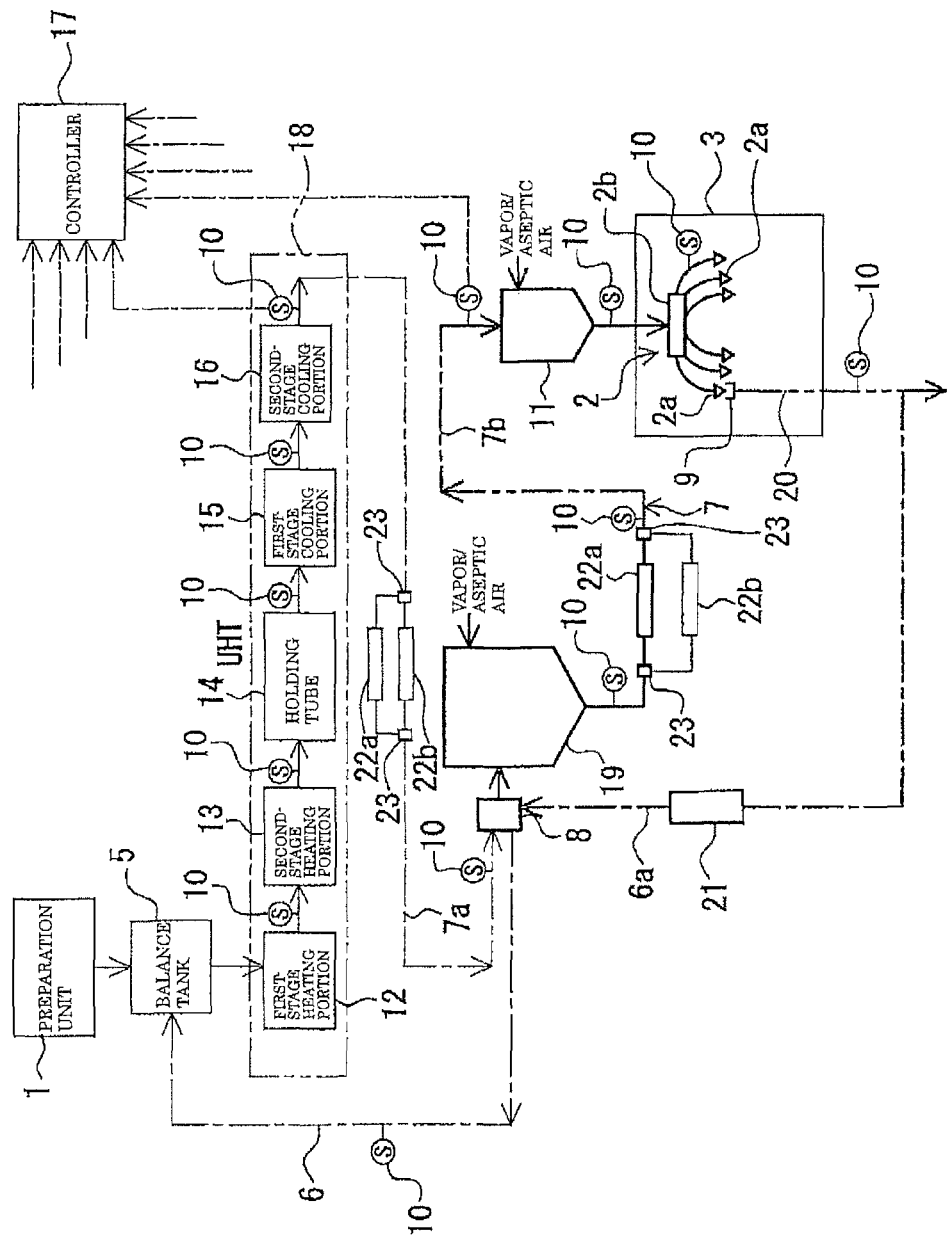
FIG. 7 is a block diagram for illustrating the CIP process or SIP process performed for a downstream-side piping section of the product supply piping between the aseptic surge tank (inclusive) and filling nozzles (inclusive) in the cleaning and sterilization method according to the second embodiment of the present invention.
Figure 8:
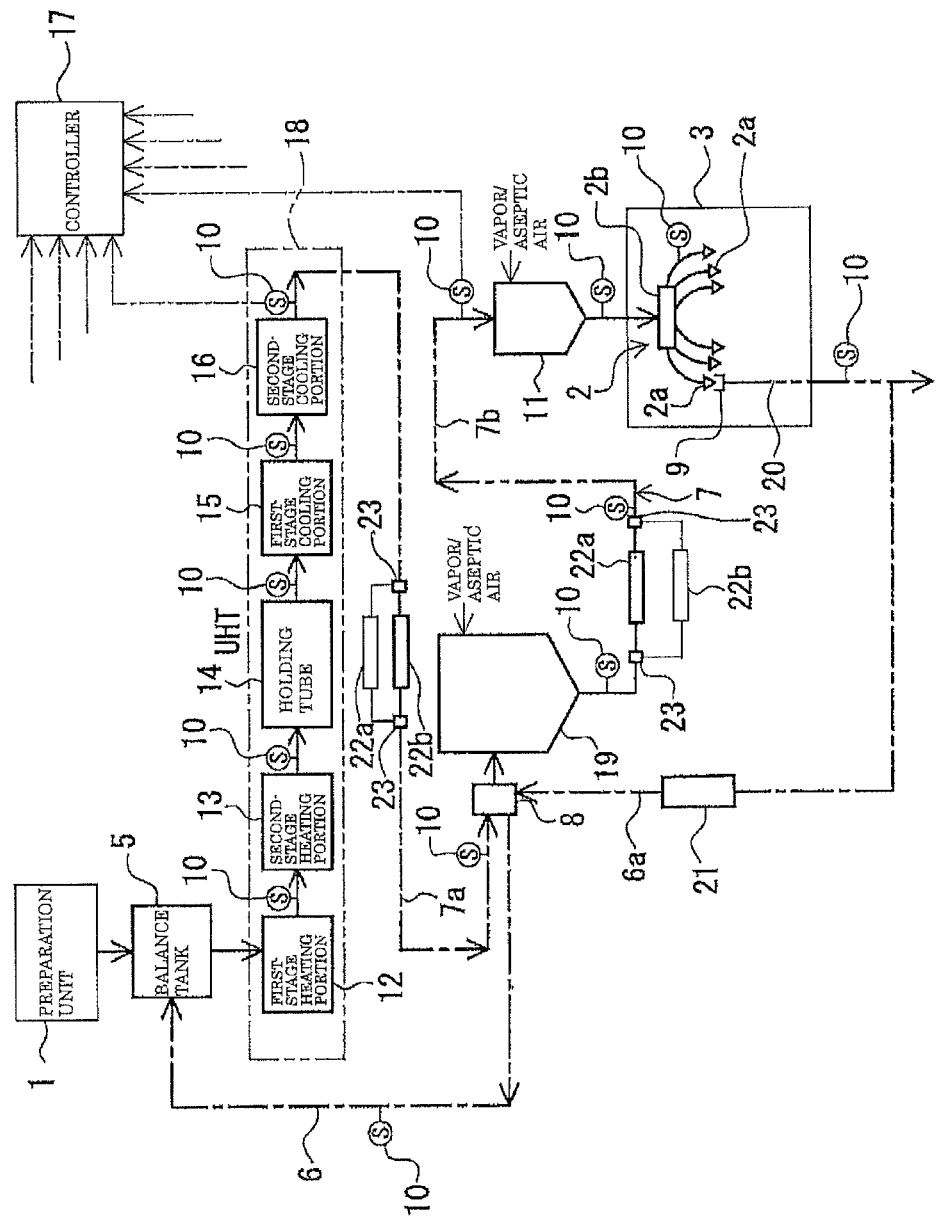
FIG. 8 is a block diagram for illustrating the CIP process performed for the entire product supply piping in the cleaning and sterilization method according to the second embodiment of the present invention.

As shown in FIG. 6, when an operation button on a panel (not shown) of the controller 17 is manipulated, the CIP process is performed for each of the upstream-side piping section 7a and the downstream-side piping section 7b of the product supply piping 7 in a predetermined procedure. The CIP process is performed by flowing an alkali cleaner that contains a mixture of water and an alkali agent such as caustic soda (sodium hydroxide), potassium hydroxide, sodium carbonate, sodium silicate, sodium phosphate, sodium hydrochloride, a surface active agent or a mixture thereof and is supplied from a cleaner supply source (not shown) and then flowing an acid cleaner that contains a mixture of water and a nitrate-based or phosphate-based acid agent and is supplied from a cleaner supply source (not shown).

The cleaners supplied from the cleaner supply sources (not shown) are activated by the UHT 18 provided for the upstream-side piping section 7a and the heating unit 21 provided for the downstream-side piping section 7b until a predetermined flowrate (1.5 m/s or higher, for example) and a predetermined temperature (80° C., for example) are reached. The cleaners are constantly or intermittently supplied in a constant amount from the respective cleaner supply sources (not shown) and remove drink residues from the previous operation on the interior of the product supply piping 7 while circulating in the product supply piping 7. The cleaners may be discharged from the apparatus as appropriate. After the cleaners are passed for a predetermined time, a rinsing step is performed to rinse the cleaners from the upstream-side piping section 7a and the downstream-side piping section 7b by passing water therethrough, and then the CIP process ends. The completion of the CIP process is managed by the controller 17, and then transition to the SIP process occurs.

(SIP Process)

When the CIP process ends, the SIP process is performed for each of the upstream-side process path and the downstream-side process path in a predetermined procedure. Before the SIP process is started, the manifold valve 8 disconnects the upstream-side piping section 7a and the downstream-side piping section 7b from each other.

The SIP process for the upstream-side process path and the SIP process for the downstream-side process path can be performed in sequence or in parallel with each other.

First, the SIP process for the upstream-side process path will be described. The liquid feeding pump used for the CIP process is not stopped, and water is fed from the water supply source (not shown) to the interior of the circulation path through the balance tank 5. The water is heated and sterilized in the UHT 18 while circulating in the circulation path. In this way, the interior of the upstream-side process path is sterilized. In this step, since the liquid feeding pump is not stopped, the temperature of the UHT 18 raised and set in the CIP process does not decrease but is further raised to a temperature for the SIP process. Thus, the temperature drop during transition from the CIP process to the SIP process can be minimized (see FIG. 10). The details of the SIP process are the same as those in the first embodiment described above and therefore will not be further described here.

When the minimum F value of the F values calculated according to the formula described above reaches a target value, it is determined that sterilization of the upstream-side piping section 7a is completed, cooling water is supplied to the first-stage cooling portion 15 and the second-stage cooling portion 16 to cool the hot water. The water supplied to rinse the cleaner needs to be sterilized in the second-stage heating portion and the holding tube with the same or higher sterilization strength as that required for the subsequent sterilization of the product content. The sterilization strength is also constantly calculated according to the above formula for determining the F value, and the F value is controlled to prevent the sterilization strength from decreasing. Alternatively, to maintain a fixed cleaning effect, the rinse water used for cleaning may be aseptic water obtained by sterilizing water at a certain temperature for a certain time (so as to have an F0 value equal to or higher than 4 or preferably equal to or higher than 30, for example). Finally, it is checked by using a conductivity meter (not shown) or the like that there is no cleaner remaining in the piping. When the cleaner is replaced by water, supply of water is stopped, and then the water continuously circulates, waiting for the start of sterilization of the drink.

After the SIP process is completed, the temperature stabilization step is performed to set the temperature and flowrate of the product supply piping for the product sterilization process for the drink. In this process, according to the sterilization temperature of the product to be manufactured, the temperature of the UHT 18 raised in the SIP process is adjusted to a set temperature for the product sterilization process (see symbols a to c in FIG. 10).

In the temperature stabilization step, the sterilization temperatures at the positions in the UHT 18 and the time required for the water to pass through the holding tube 14 are recorded at intervals of 1 second. The temperature data and the flowrate data are transmitted to the controller 17 and stored. The temperature data and the flowrate data are preferably recorded for a period of time (for example, 200 seconds) that is three or four times as long as the passing time of the holding tube 14 (for example, 60 seconds), because such a length of time allows calculation of the actual strength of the sterilization of the content having passed through the holding tube 14.

Figure 19:
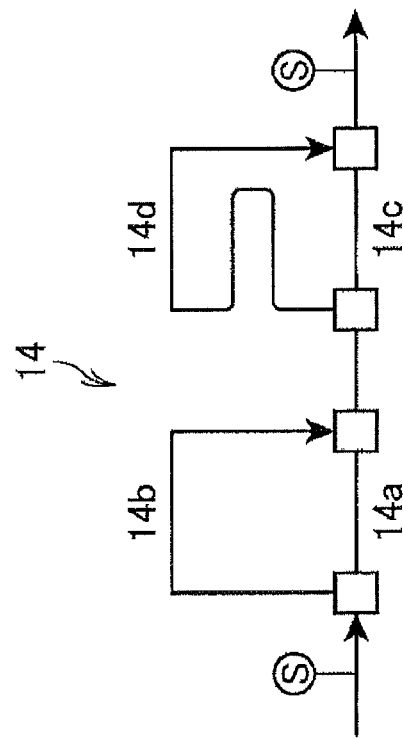
FIG. 19 is a diagram for illustrating details of a holding tube.
Figure 20:
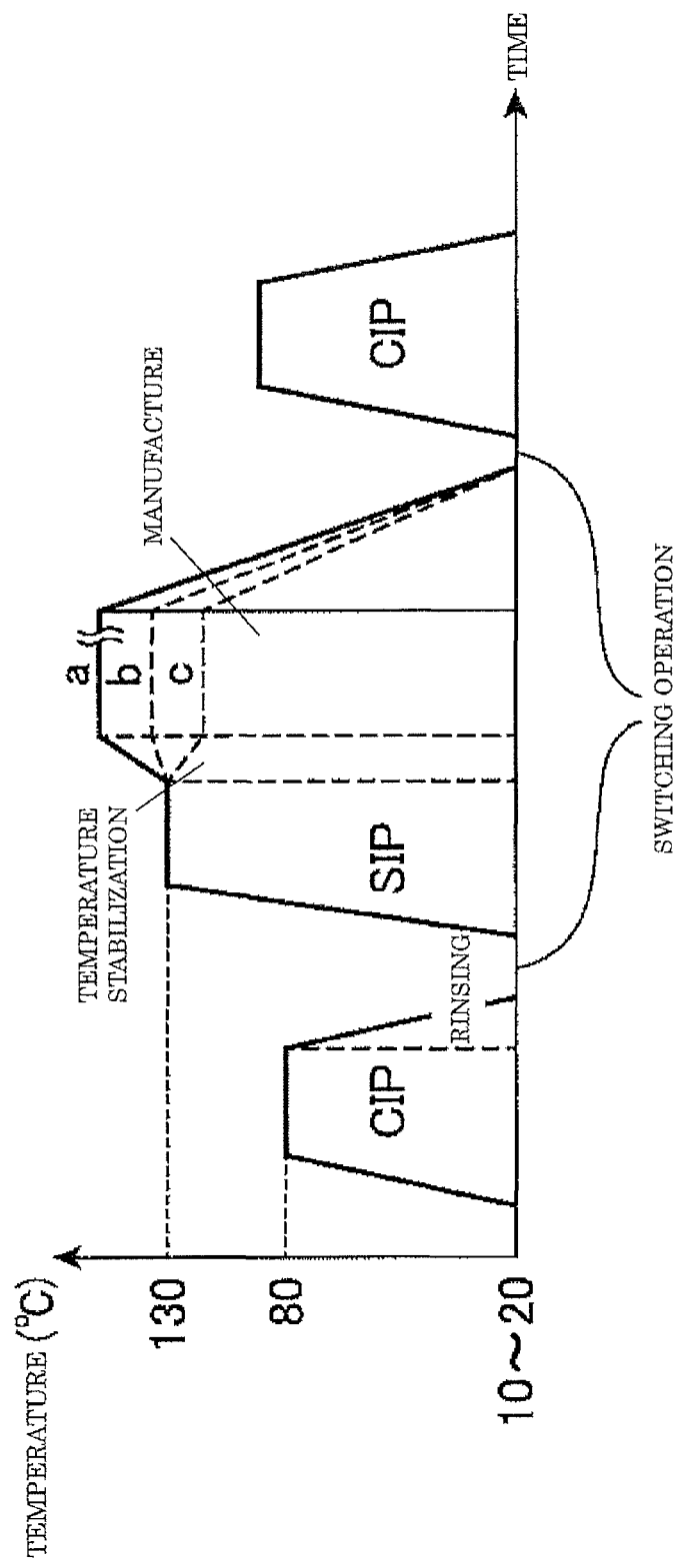
FIG. 20 is a graph for illustrating a variation in temperature in the CIP process, the SIP process and the manufacturing step in a conventional cleaning and sterilization method.

As an alternative to the method of changing the F value to change the sterilization condition for the product according to the kind of the product, the sterilization condition may be changed by modifying the length of the holding tube to adjust the length of time for which the product flows in the holding tube, thereby changing the sterilization temperature achieved by heating and the holding time. In this case, if the length of the holding tube is switched between two or more lengths (if the holding time is switched between 30 seconds and 60 seconds, for example), sterilization conditions for various products can be achieved. Specifically, as shown in FIG. 19, the holding tube has a first pipe line 14a, a second pipe line 14b, a third pipe line 14c and a fourth pipe line 14d, and the total length of the holding tube can be adjusted by changing the combination of pipe lines by switching valves. Since the CIP process and the SIP process are performed at the same time or in sequence, the length of the holding tube is preferably changed by automatic valves while considering the safe back pressure. Furthermore, since the CIP process and the SIP process are performed at the same time or in sequence, all the pipe lines of the holding tube can be cleaned and sterilized during the CIP process and the SIP process, and then, the pattern of the holding tube can be changed for the subsequent production. If there is a pipe line of the holding tube that is not used, after the SIP process, aseptic air can be supplied to the pipe line to keep the pipe line at a positive pressure in an aseptic condition. Alternatively, blow valves for drainage may be provided as the end valves of the pipe lines of the holding tube, and the pressure in any pipe line that is not used may be reduced to zero. Alternatively, to prevent contamination by bacteria from outside, a vapor barrier may be provided in the valves at the opposite ends of the pipe lines of the holding tube.

Figure 11:
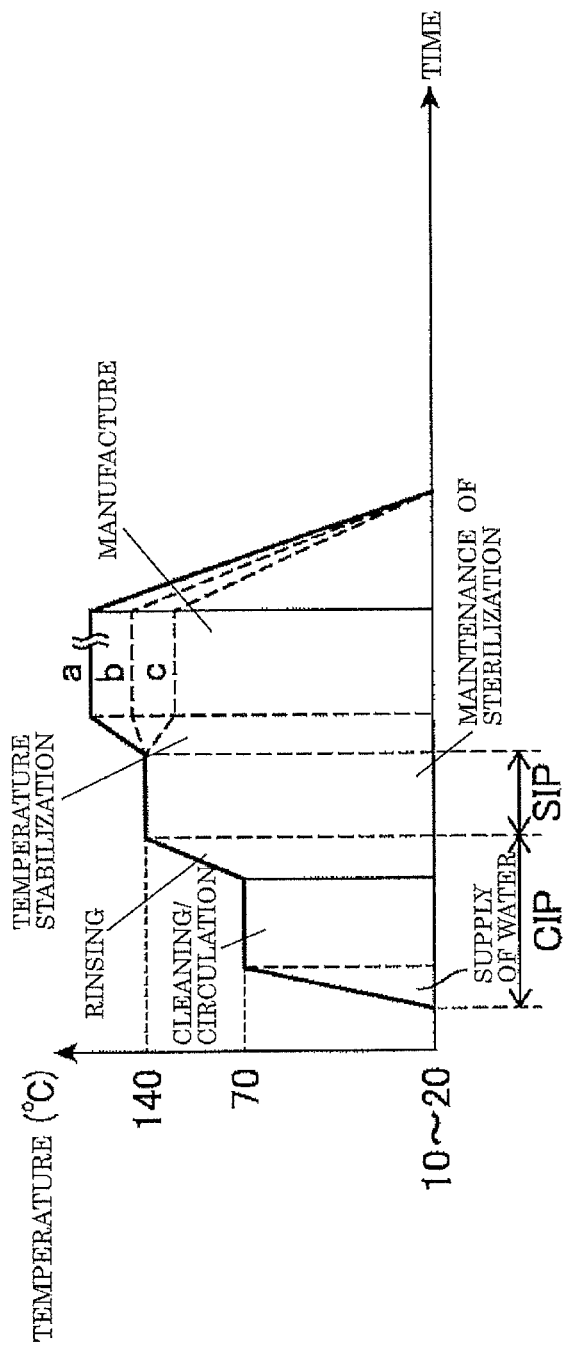
FIG. 11 is a graph for illustrating another variation in temperature of the upstream-side piping section in the CIP process, the SIP process and the manufacturing step in the cleaning and sterilization method according to the second embodiment of the present invention.
Figure 12:
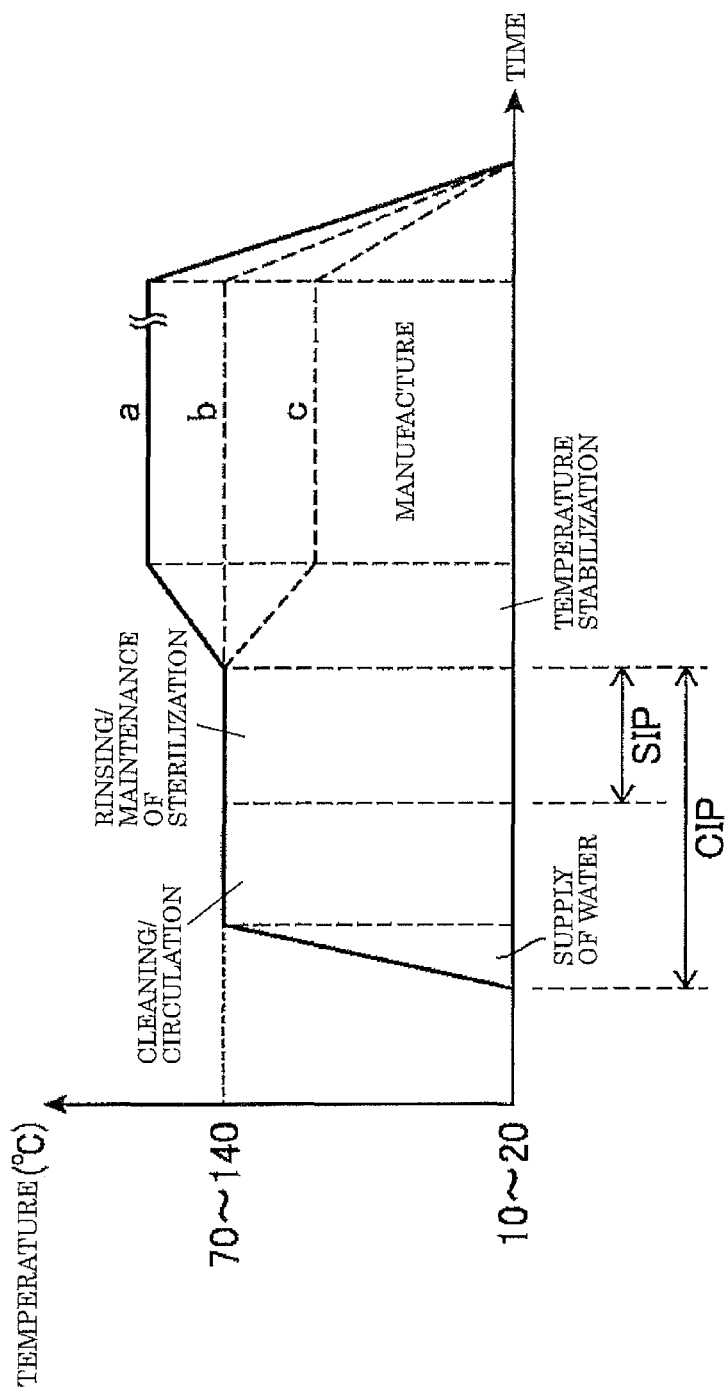
FIG. 12 is a graph for illustrating another variation in temperature of the upstream-side piping section in the CIP process, the SIP process and the manufacturing step in the cleaning and sterilization method according to the second embodiment of the present invention.
Figure 13:
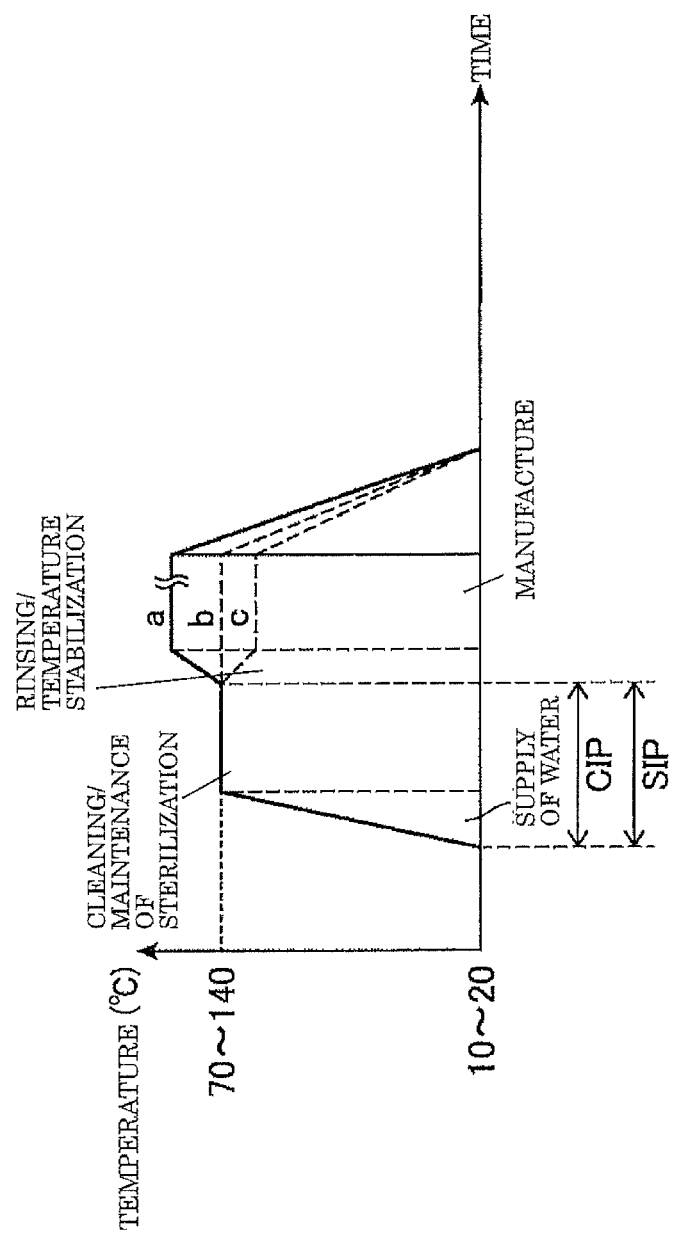
FIG. 13 is a graph for illustrating a variation in temperature of the upstream-side piping section in the manufacturing step in the cleaning and sterilization method according to the second embodiment of the present invention in a case where the CIP process and the SIP process are performed at the same time.

The step of rinsing the cleaner used in the CIP process that is performed in transition from the CIP process to the SIP process can be performed while increasing the temperature from the temperature at which the CIP process has been performed to the temperature at which the SIP process is to be performed as shown in FIG. 11. The rinse water used in this rinsing step is heated in the UHT 18. To maintain the flowrate while maintaining the aseptic condition in the rinsing step, a heat exchanger is preferably arranged before the balance tank 5 to reduce the cooling efficiency of the first-stage cooling portion 15 and the second-stage cooling portion 16 so that the temperature of the rinse water entering the balance tank 8 is raised by the waste heat of the rinse water discharged after rinsing. With such a configuration, even if the flowrate of the rinse water increases, the temperature of the rinse water can be raised in the UHT 18 with reliability, so that the rinsing step can be effectively performed in a shorter time. If water that achieves the sterilization strength for the subsequent product is used in the rinsing step, the rinsing step can be performed during the SIP process as shown in FIG. 12, or performed during the temperature stabilization step following the SIP process as shown in FIG. 13. What is essential is that the cleaner is removed before the subsequent manufacturing process is started. Furthermore, as shown in FIG. 13, the SIP process may be performed at the same time as the CIP process using an alkali or acid that satisfies the sterilization temperature condition, and the manufacture of the subsequent product may be started after the interior of the piping is cleaned with aseptic water having at least a sterilization strength prescribed for the subsequent product and the cleaner is removed.

When or before the SIP process for the upstream-side piping section 7a is started, the SIP process for the downstream-side process path including the aseptic surge tank 19 is started. The SIP process for the downstream-side process path is the same as that in the first embodiment described above and therefore will not be described in detail here.

Figure 14:
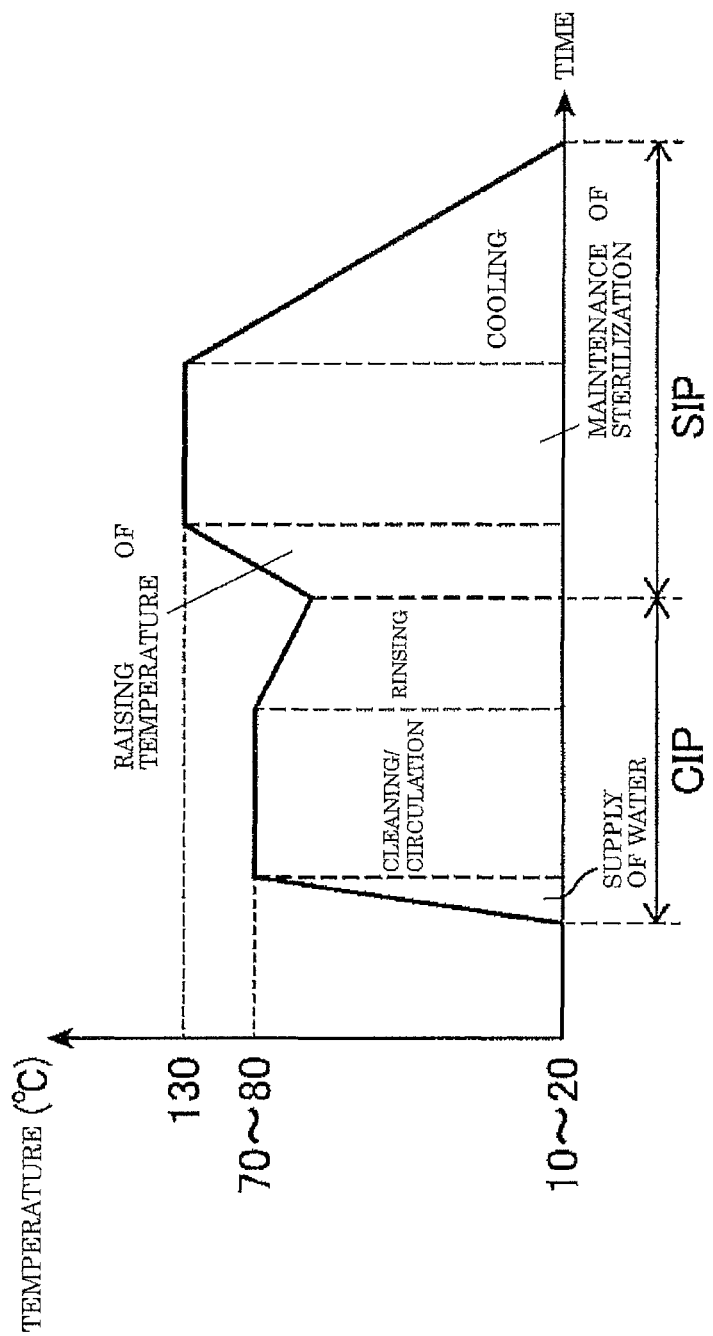
FIG. 14 is a graph for illustrating a variation in temperature of the downstream-side piping section in the CIP process, the SIP process and the manufacturing step in the cleaning and sterilization method according to the second embodiment of the present invention.

After the SIP process, aseptic air, aseptic water or the product is fed into the downstream-side piping section 7b to cool the interior of the downstream-side piping section 7b to, for example, room temperature as shown in FIG. 14. Then, the drain tubes 20 are disconnected. Furthermore, the actuator (not shown) removes the cups 9 from the openings of the filling nozzles 2a. The aseptic water may be fed from the product sterilizer that has finished the SIP process for the downstream-side process path and is in the water operation in the standby state. Alternatively, aseptic water (not shown) may be received through the manifold valve 8 and used for cooling. The cooling with the aseptic water can be started after the temperature of the tank after the SIP process has been reduced to below 110° C. (preferably to below 100° C.) by cooling with the aseptic air. The operation of supplying the aseptic water is performed under pressure by supplying aseptic air to prevent the pressure in the tank from decreasing due to rapid cooling by using an intermittent timer. After the temperature of the tank has decreased to about 30 to 90° C., and the cooling is completed, the aseptic water remaining in the tank and the piping is blown off by aseptic air while maintaining a positive pressure, and the product is received. Alternatively, the cooling with the aseptic water may be omitted, and the product may be received immediately after the SIP process. By additionally using the aseptic water or the product for cooling as described above, the cooling can be achieved in a shorter time than when only air is used for cooling. The tank may be quickly cooled by supplying water or chiller water to a jacket of the tank in parallel with the cooling process described above. In the cooling step with the aseptic air in the SIP process, the blow valves may be sequentially closed at positions where the cooling completion temperature is reached to efficiently feed the cooling aseptic air to parts that are more difficult to cool.

If the drink to be manufactured next is a carbonated drink, the aseptic water is fed from a vicinity of the aseptic surge tank 19 to the head tank 11 and the filling nozzles 2a through a carbonated drink line (not shown). On the carbonated drink line, the aseptic water is further cooled (to 1 to 5° C.) by chiller water. Thus, the remaining heat from the SIP process can be completely removed, and foaming of the carbon dioxide gas can be reduced during filling.

Figure 15:
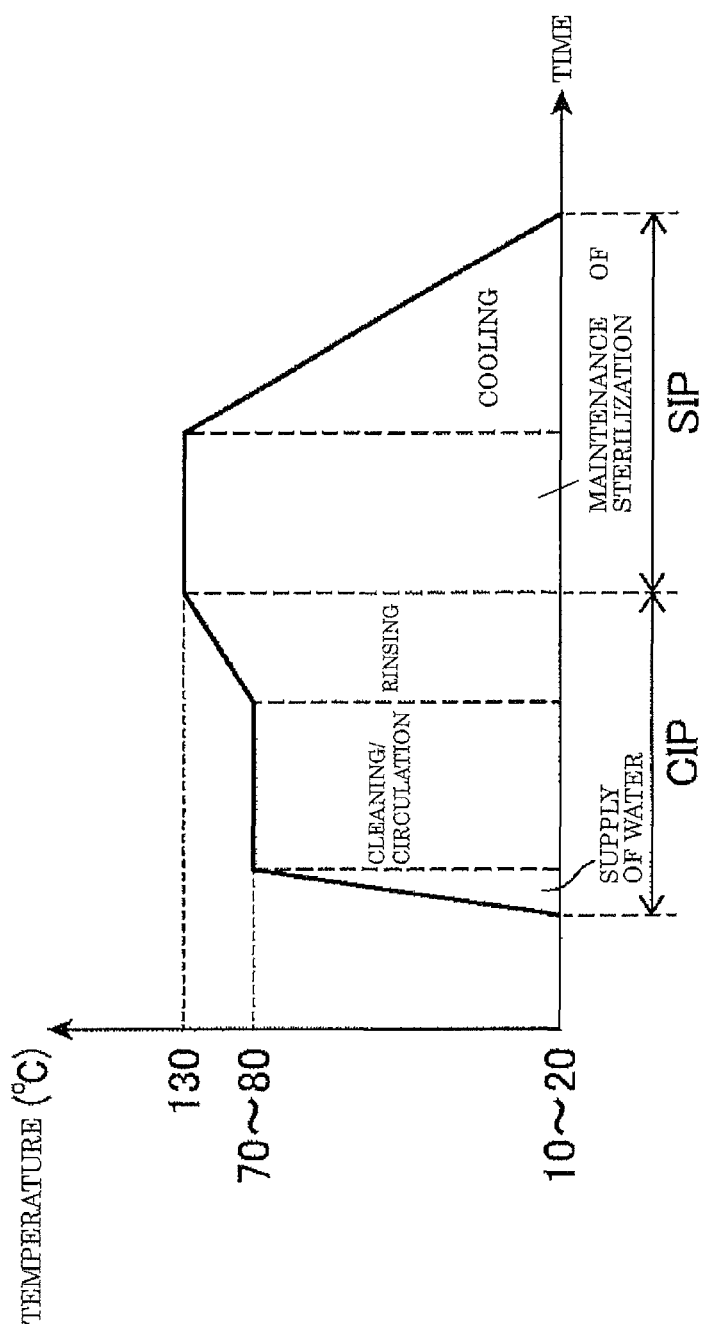
FIG. 15 is a graph for illustrating another variation in temperature of the downstream-side piping section in the CIP process, the SIP process and the manufacturing step in the cleaning and sterilization method according to the second embodiment of the present invention.
Figure 16:
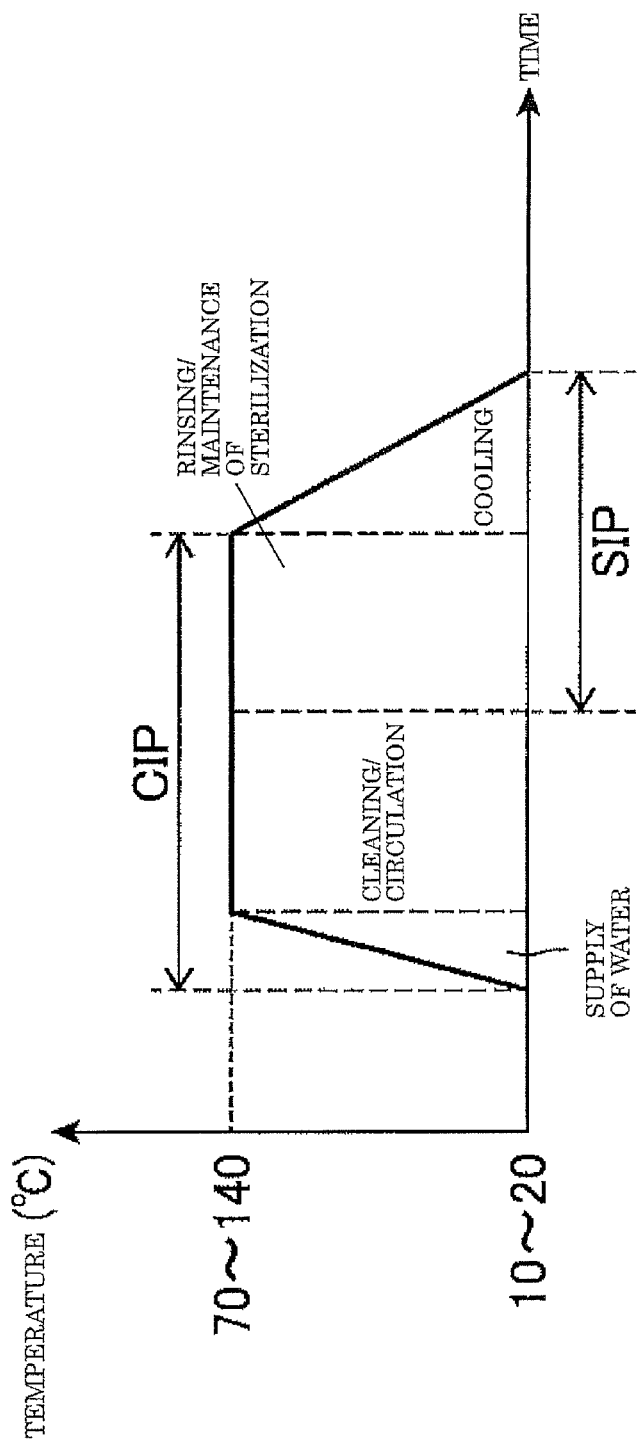
FIG. 16 is a graph for illustrating another variation in temperature of the downstream-side piping section in the CIP process, the SIP process and the manufacturing step in the cleaning and sterilization method according to the second embodiment of the present invention.
Figure 17:
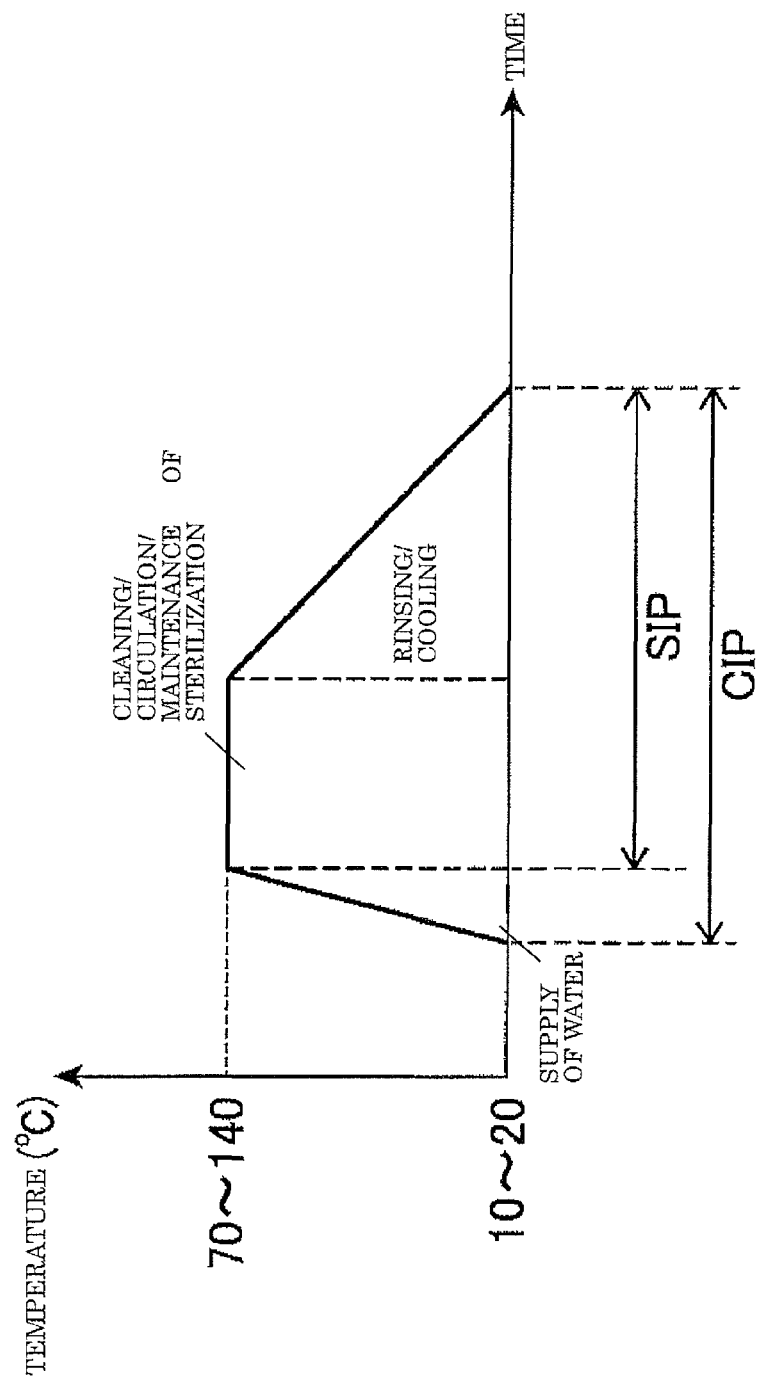
FIG. 17 is a graph for illustrating another variation in temperature of the downstream-side piping section in the CIP process, the SIP process and the manufacturing step in the cleaning and sterilization method according to the second embodiment of the present invention.
Figure 18:
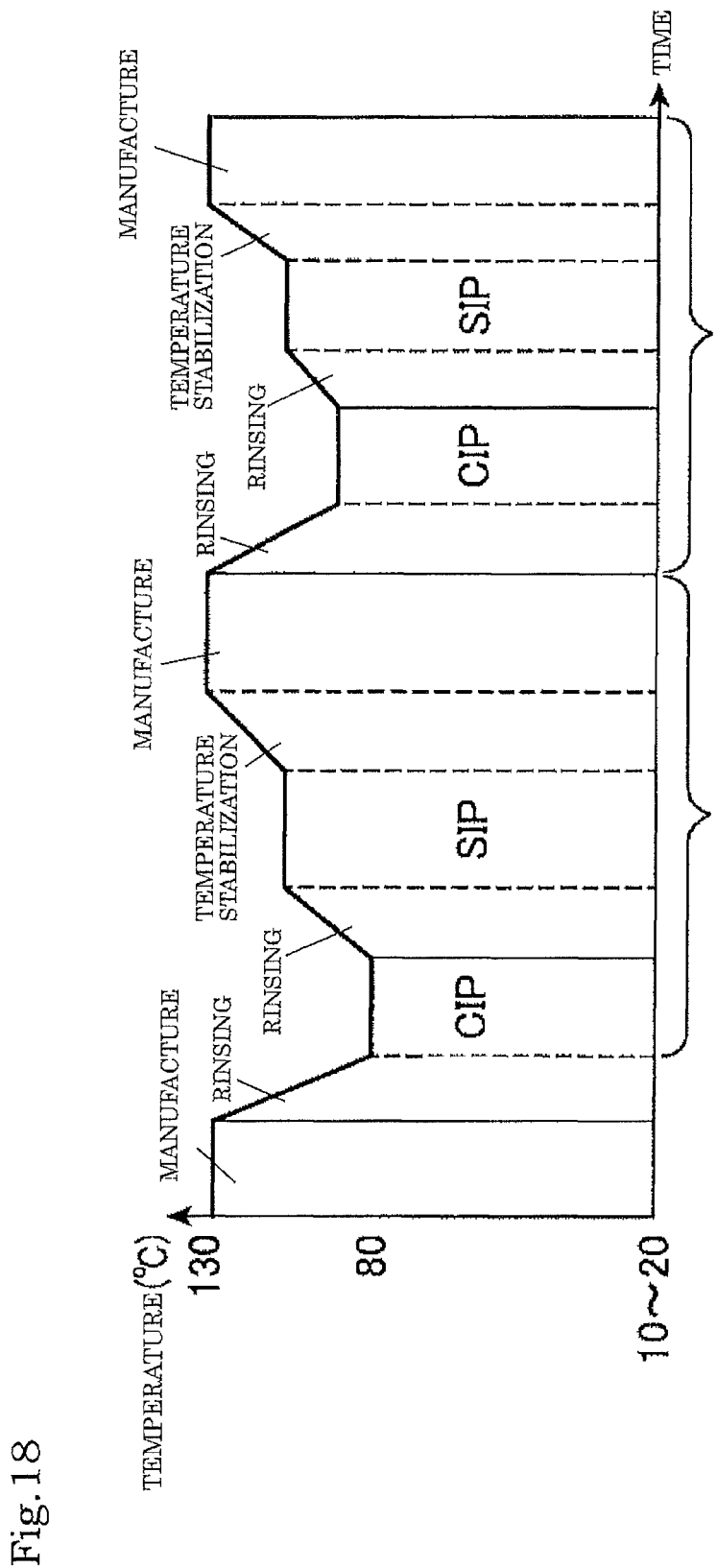
FIG. 18 is a graph for illustrating a variation in temperature in the CIP process, the SIP process and the manufacturing step in the cleaning and sterilization method according to the second embodiment of the present invention in a case where different products are manufactured in sequence.

As with the case of the upstream-side piping section described above, the step of rinsing the cleaner used in the CIP process that is performed in transition from the CIP process to the SIP process can be performed while increasing the temperature from the temperature at which the CIP process has been performed to the temperature at which the SIP process is to be performed as shown in FIG. 15. If water that achieves the sterilization strength for the subsequent product is used in the rinsing step, the rinsing step can be performed during the SIP process as shown in FIG. 16, or performed during the cooling step following the SIP process as shown in FIG. 17. What is essential is that the cleaner is removed before the subsequent manufacturing process is started. Furthermore, as shown in FIG. 17, the SIP process may be performed at the same time as the CIP process using an alkali or acid that satisfies the sterilization temperature condition, and the manufacture of the subsequent product may be started after the interior of the piping is cleaned with aseptic water having at least a sterilization strength prescribed for the subsequent product and the cleaner is removed.

To perform the SIP process for one of the upstream-side process path and the downstream-side process path while performing the CIP process for the other, a valve unit (with a vapor barrier) that allows steam to pass therethrough is preferably provided at an intersection between both the paths in the manifold valve 8. In that case, even if a valve fails on one of the process paths, the risk of contamination of the interior of the other path is reduced. Alternatively, aseptic water can be used instead of the steam, or risks that may occur when a valve fails can be reduced by arranging a plurality of valves at the intersection of the process paths.

(Manufacturing Step)

After the SIP process for the aseptic surge tank 19 and the following part of the downstream-side piping section 7b ends, the drink flowing from the UHT 18 through the upstream-side piping section 7a is stored in the aseptic surge tank 19, and a manufacturing step of filling the bottles 4 with the drink flowing therefrom through the downstream-side piping section 7b is started.

Figure 9:
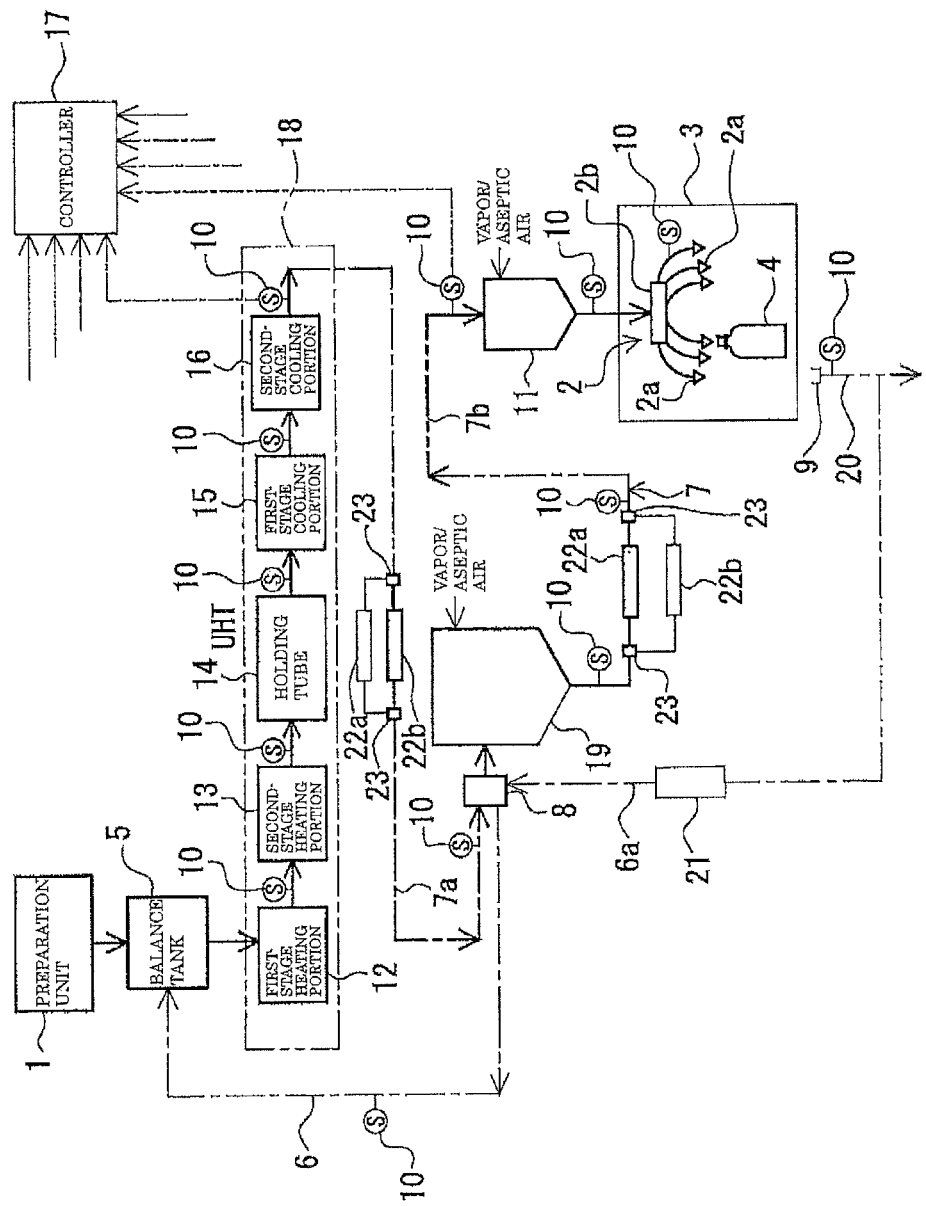
FIG. 9 is a block diagram for illustrating production of a bottled product.
Figure 10:
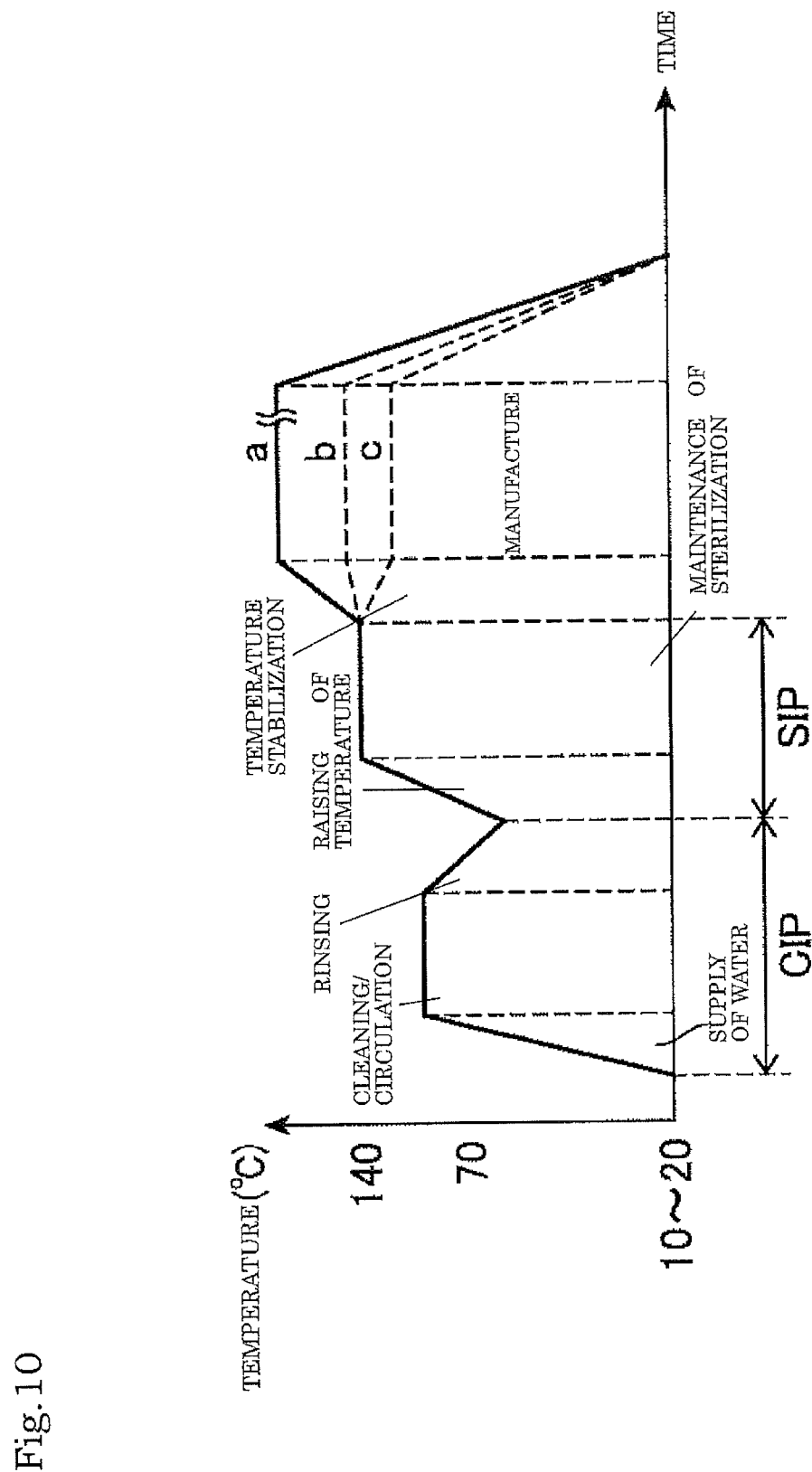
FIG. 10 is a graph for illustrating a variation in temperature of the upstream-side piping section in the CIP process, the SIP process and a manufacturing step in the cleaning and sterilization method according to the second embodiment of the present invention.

As shown by a bold line in FIG. 9, in the manufacturing step, the product prepared in the preparation unit 1 flows to the interior of the filling machine 2 through the sterilized upstream-side piping section 7a and downstream-side piping section 7b of the product supply piping 7, and the bottles 4 as containers are filled with the product through the filling nozzles 2a in the filling machine 2. The bottles 4 filled with the product are capped by a capper (not shown) and then fed out of the filling machine 2.

After the manufacturing step is completed, a second manufacturing step can be continuously performed to manufacture a different kind of product than the previous product. In that case, the product supply piping 7 needs to be cleaned and sterilized in the same processes as the CIP and SIP processes described above. However, before starting the CIP process of the second manufacturing step, a transition from the set temperature of the UHT 18 in the first manufacturing step to the set temperature for the CIP process is preferably made while performing the rinsing process of passing water, aseptic water or the like through the product supply piping 7 (see FIG. 18).

Figure 5:
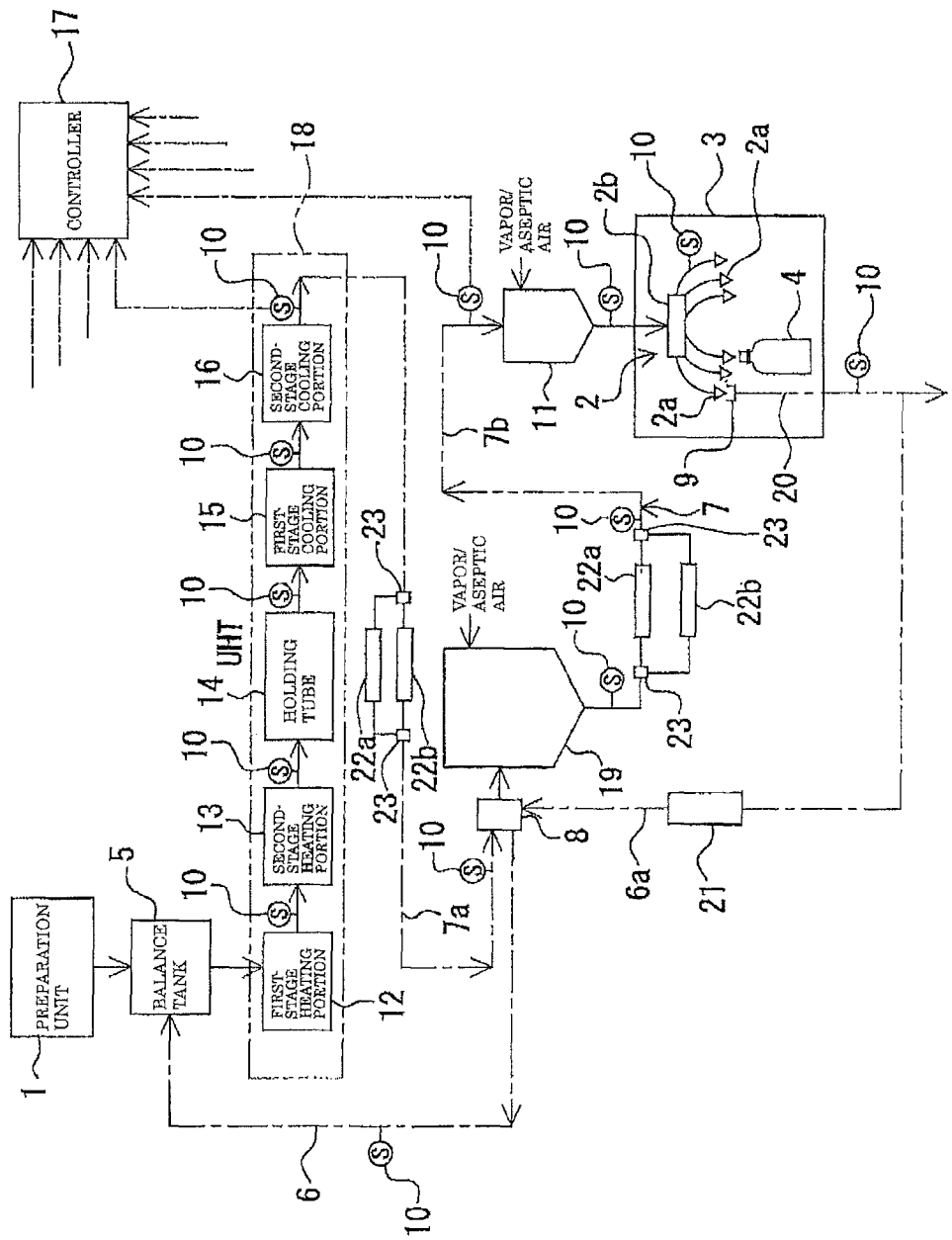
FIG. 5 is a block diagram showing a product filling apparatus that performs a cleaning and sterilization method according to a second embodiment of the present invention.

As shown in FIG. 5, the product supply piping 7 is preferably provided with a filtering device that filters out foreign matters in the product. The filtering device includes a first filtering device and a second filtering device arranged in parallel with each other, and the first and second filtering devices include a filtering member formed by a metal filter, such as a stainless steel filter. The filtering device further includes switching devices 23, 23 that automatically or manually switch between the first filtering device 22a and the second filtering device 22b.

The first filtering device 22a and the second filtering device 22b are preferably metal filters such as stainless steel filters and preferably differ in mesh fineness (mesh size). Preferably, for example, the first filtering device 22a includes a metal filter of 100 to 400 mesh capable of removing finer foreign matters, and the second filtering device 22b includes a rougher metal filter of 10 to 100 mesh capable of appropriately allowing flesh or pulp in the product to pass therethrough. By using filtering devices of different counts for the first filtering device 22a and the second filtering device 22b as described above, foreign matters can be appropriately removed from each individual product to be manufactured.

In addition, the switching devices 23, 23 allow switching between the first filtering device 22a and the second filtering device 22b. Since the switching devices 23, 23 are provided, while the first filtering device 22a is being used for filling with the product as shown in FIG. 9, a cleaning step for the second filtering device 22b can be performed to remove foreign matters from the second filtering device 22b. Thus, during manufacture of the product, the filtering device can be efficiently cleaned and inspected. After the cleaning and inspection of the filters, the CIP process or the SIP process can be separately performed. The switching devices 23 can be set to feed liquid to both the first filtering device 22a and the second filtering device 22b. In that case, the CIP process or the SIP process for both the first filtering device 22a and the second filtering device 22b can be performed at the same time. To reduce the risk of contamination of the product by a chemical agent or bacteria, the vapor barrier described above may be provided in the switching devices 23.

As shown in FIG. 5, for example, the filtering device may be disposed between the second-stage cooling portion (final cooling portion) 16 and the manifold valve 8, rather than being disposed between the aseptic surge tank 19 and the head tank 11. A plurality of filtering devices arranged in parallel with each other may be provided. The filtering device may be disposed at different positions, such as at a position upstream of the balance tank 5 or at the tip ends of the filling nozzles.

As described above, the first filtering device and the second filtering device are arranged in parallel with each other in the filtering device. Therefore, for example, filtering of the product can be performed by the first filtering device when the product is manufactured in the first manufacturing step, and can be performed by the second filtering device when the product is manufactured in the second manufacturing step. In that case, while the product is being manufactured, the filtering device that is not used for filtering of the product is preferably subjected to a cleaning step of removing remaining foreign matters from the manufacturing step and an inspection operation of checking that the product does not contain rubber or metal foreign matters such as a gasket residue. By performing the cleaning operation and the inspection operation during manufacture of the product as described above, a cleaned filtering device can always be used after transition from the first manufacturing step to the second manufacturing step, and the operability of the product filling apparatus is improved.

As described above with regard to the F value, sterilization conditions suitable for various kinds of drinks can be satisfied by changing the flowrate and temperature of the fluid. However, in the CIP process, the flowrate is generally higher than in the manufacture of the product, so that the temperature needs to be reduced in order to maintain the F value, and thus it is difficult to achieve high temperature. For this reason, when an existing facility is used, the CIP process can be performed by reducing the flowrate as far as cleaning can be achieved. Alternatively, the existing facility may be improved by increasing the number of stages of heating portions or extending the length of the heating part to enhance the heating capability. Alternatively, the cooling capability during the CIP process may be reduced by adjusting the settings of the cooling part so that the required sterilization temperature can be achieved by the heating part even if the flowrate increases.

Although the present invention is configured as described above, the present invention is not limited to the embodiments described above, and various modifications can be made within the scope of the spirit of the present invention. The manifold 8 may be omitted, and the CIP and SIP processes for the components from the sterilizer to the filler can be performed at the same time, and control of the temperature stabilization step described above can also be performed. Alternatively, the SIP process may be performed at the same time as the CIP process using an alkali or acid that satisfies the sterilization temperature condition, and the manufacture of the subsequent product may be started after the interior of the piping is cleaned with aseptic water having at least a sterilization strength prescribed for the subsequent product and the cleaner is removed. Although the aseptic surge tank and the head tank in the downstream-side piping section 7b are subjected to the CIP process and the SIP process at the same time in the second embodiment described above, the aseptic surge tank and the head tank can be separately subjected to the CIP process and the SIP process. In that case, the amount of the liquid residing in the piping is reduced, and the CIP process and the SIP process can be completed in a shorter time. Although, in this specification, a shell and tube type heat exchanger has been described as an example of the UHT (heating sterilization part) according to the present invention, the UHT is not limited to this type, and a plate type heat exchanger can also be used, for example. Furthermore, not only these indirect heating schemes but also direct heating schemes can be used. Furthermore, the present invention has been described with regard to the drink filling apparatus used for filling with a drink as a product, the product is not limited to drinks, and the drink filling apparatus can be applied to filling with a medicine, a food, a liquid food or a drink containing a solid material. Furthermore, although the transition from the CIP process to the SIP process has been described with regard to a case where the temperature for the SIP process is higher than the set temperature for the CIP process, the CIP process and the SIP process may be performed at the same temperature, or the CIP process may be performed at a higher temperature than the SIP process. Although the water used for the CIP process is typically tap water, when the CIP process is performed at a temperature higher than 90° C. in order to perform the SIP process at the same time, pure water is preferably used instead of tap water in order to prevent calcium deposition.

The time interval at which the F value is measured and integrated is not limited to 1 minute but can be 1 to 5 seconds. The time interval can be changed depending on the capability of the measuring instrument or the like.

In the first embodiment and the second embodiment described above, for the ease of explanation, the invention according to the first embodiment and the invention according to the second embodiment have been separately described. However, these embodiments can also be combined with each other.

REFERENCE NUMERALS 2 filling machine
6 feedback path 7 product supply piping
7a upstream-side piping section
7b downstream-side piping section
18 heating sterilization part

The invention claimed is:

1. A sterilization process transition method of switching from an SIP process to a product sterilization process in a product filling apparatus that includes product supply piping that feeds a product into a filling machine through a heating sterilization part, the SIP process being intended to sterilize the product supply piping in advance before a product filling operation, and the product sterilization process being intended to sterilize the product to be filled, the method comprising:
  calculating an F value from temperature data and flowrate data on a fluid flowing in the heating sterilization part that are obtained from a plurality of temperature sensors and flowmeters disposed at arbitrary positions in the product filling apparatus at predetermined time intervals, and
  adjusting the temperature and flowrate at two or more of the plurality of predetermined positions in the product filling apparatus from a set temperature and a set flowrate for the SIP process to a set temperature and a set flowrate for the product sterilization process while preventing the F value from becoming lower than a predetermined value.

2. The sterilization step transition method according to claim 1, wherein a pressure of the product passing through the heating sterilization part is higher than a pressure of a heat source that heats the heating sterilization part or a pressure of a coolant that cools the heating sterilization part.

3. The sterilization process transition method according to claim 1, wherein the F value is calculated according to $$F=\int_{t_0}^{t_1}10^{(T-Tr)/Z}dt \quad \text{[formula 1]}$$

where T denotes an arbitrary sterilization temperature (° C.), $10^{(T-Tr)/Z}$ represents a fatality rate at an arbitrary temperature T, Tr denotes a reference temperature r (° C.), and Z denotes a Z value (° C.).

4. A product filling apparatus comprising product supply piping that feeds a product into a filling machine through a heating sterilization part and a sterilization process transition unit that switches from an SIP process to a product sterilization process, the SIP process being intended to sterilize the product supply piping in advance before a product filling operation, and the product sterilization process being intended to sterilize the product to be filled,
  wherein the product filling apparatus further comprises a controller that calculates an F value from temperature data and flowrate data on a fluid flowing in the heating sterilization part that are obtained from a plurality of temperature sensors and flowmeters disposed at arbitrary positions in the product filling apparatus at predetermined time intervals, and adjusts the temperature and flowrate at two or more of the plurality of predetermined positions in the product filling apparatus from a set temperature and a set flowrate for the SIP process to a set temperature and a set flowrate for any one of the product sterilization processes while preventing the F value from becoming lower than a predetermined value.

5. A method of cleaning and sterilizing a product filling apparatus that includes product supply piping that feeds a product into a filling machine through a heating sterilization part, the method comprising a CIP process of removing a remaining foreign matter from a product or the like on an interior of the product supply piping and an SIP process of sterilizing the interior of the product supply piping, wherein
  the CIP process and the SIP process are performed in sequence without an interruption between the CIP process and the SIP process, and
  a temperature of a heating sterilization part (UHT) raised and set in the CIP process is not decreased but is further raised to a temperature for the SIP process, or a step of rinsing a cleaner, which is used in the CIP process, is performed in transition from the CIP process to the SIP process while increasing the temperature at which the CIP process has been performed to the temperature at which the SIP process is to be performed.

6. The method of cleaning and sterilizing a product filling apparatus according to claim 5, wherein the SIP process ends when an F value reaches a predetermined value, the F value being determined by substituting a value obtained from a thermometer in the product supply piping into the following formula:

$$F=\int_{t_0}^{t_1}10^{(T-121.1)/10}dt \quad \text{[formula 2]}$$

where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

7. The method of cleaning and sterilizing a product filling apparatus according to claim 5, wherein rinse water used to rinse the cleaner used in the CIP process has a sterilization strength determined from a sterilization temperature of the heating sterilization part and a flowrate in the heating sterilization part.

8. A method of cleaning and sterilizing a product filling apparatus that includes product supply piping that feeds a product into a filling machine through a heating sterilization part, the method comprising:
  a CIP process of removing a remaining foreign matter from a product or the like on an interior of the product supply piping and an SIP process of sterilizing the interior of the product supply piping,
  wherein the CIP process and the SIP process are performed in sequence without an interruption between the CIP process and the SIP process;
  a first manufacturing step of performing a filling step of filling a container with the product while performing a product sterilization process after the SIP process; and
  a second manufacturing step including the CIP process and the SIP process for manufacturing a product different from that manufactured in the first manufacturing step,
  wherein the first manufacturing step and the second manufacturing step are performed without reducing the temperature of the heating sterilization part to be equal to or lower than a set temperature of the CIP process.

9. The method of cleaning and sterilizing a product filling apparatus according to claim 8, wherein the product supply piping is provided with a filtering device that filters the product, and
  the filtering device includes a switching step of switching between a first filtering device used in at least the first manufacturing step and a second filtering device used in the second manufacturing step.

10. The method of cleaning and sterilizing a product filling apparatus according to claim 9, wherein the first manufacturing step includes a cleaning step of removing a remaining foreign matter on the second filtering device.

11. A product filling apparatus that comprises product supply piping that feeds a product into a filling machine through a heating sterilization part and performs a CIP process of removing a remaining foreign matter from a product or the like on an interior of the product supply piping and an SIP process of sterilizing the interior of the product supply piping, wherein
    the CIP process and the SIP process are performed in sequence without an interruption between the CIP process and the SIP process, and
  a temperature of a heating sterilization part (UHT) raised and set in the CIP process is not decreased but is further raised to a temperature for the SIP process, or a step of rinsing a cleaner, which is used in the CIP process, is performed in transition from the CIP process to the SIP process while increasing the temperature at which the CIP process has been performed to the temperature at which the SIP process is to be performed.

* * * * *